United States Patent
Bochenko et al.

(10) Patent No.: US 8,355,753 B2
(45) Date of Patent: Jan. 15, 2013

(54) MEDICATION INJECTION SITE AND DATA COLLECTION SYSTEM

(75) Inventors: Walter John Bochenko, Encinitas, CA (US); Shawn Wayne DeKalb, San Diego, CA (US); Winthrop De Childers, San Diego, CA (US)

(73) Assignee: CRISI Medical Systems, Inc., San Diego, CA (US)

(*) Notice: Subject to any disclaimer, the term of this patent is extended or adjusted under 35 U.S.C. 154(b) by 224 days.

(21) Appl. No.: 12/765,707

(22) Filed: Apr. 22, 2010

(65) Prior Publication Data

US 2011/0111794 A1  May 12, 2011

Related U.S. Application Data

(63) Continuation-in-part of application No. 12/614,276, filed on Nov. 6, 2009.

(51) Int. Cl.
  *H04W 88/02* (2009.01)
(52) U.S. Cl. .......... 455/556.1; 604/93.01; 604/404
(58) Field of Classification Search ............ 128/203.12, 128/204.18; 361/724; 455/556.1; 600/301, 600/323, 485, 523, 532; 604/65–68, 93.01, 604/151–155, 404; 702/50, 188
See application file for complete search history.

(56) References Cited

U.S. PATENT DOCUMENTS

| | | | |
|---|---|---|---|
| 4,650,475 A | 3/1987 | Smith et al. | |
| 4,853,521 A | 8/1989 | Claeys et al. | |
| 4,978,335 A | 12/1990 | Arthur, III | |
| 5,279,576 A | 1/1994 | Loo et al. | |
| 5,628,309 A | 5/1997 | Brown | |
| 5,651,775 A | 7/1997 | Walker et al. | |
| 5,692,640 A | 12/1997 | Caulfield et al. | |
| 5,782,814 A | 7/1998 | Brown et al. | |
| 5,792,117 A | 8/1998 | Brown | |
| 5,873,731 A | 2/1999 | Prendergast | |
| 5,984,901 A | 11/1999 | Sudo et al. | |

(Continued)

FOREIGN PATENT DOCUMENTS

DE 29617777 U1 12/1996

OTHER PUBLICATIONS

International Search Report dated Aug. 2, 2011 for corresponding PCT Application No. PCT/US2010/055322.

*Primary Examiner* — Nicholas Lucchesi
*Assistant Examiner* — Gerald Landry, II
(74) *Attorney, Agent, or Firm* — Mintz, Levin, Cohn, Ferris, Glovsky and Popeo, P.C.

(57) ABSTRACT

A medication injection site is provided that includes a medication port and an identification sensor. The medication injection site, when coupled to a medication container, can wirelessly transmit data characterizing the contents of the medication container to a remote data collection system. The housing of the medication injection site has a shape and size enabling it to be held by a first hand of a user while the user administers medication from the medication container via the medication port using his or her second hand. The housing can include a disposable sub-housing and a reusable sub-housing such that the reusable sub-housing is used by many patients. In some implementations, the medication injection site can be placed on an IV drip line. Related apparatus, systems, and kits are also disclosed.

34 Claims, 19 Drawing Sheets

U.S. PATENT DOCUMENTS

| | | |
|---|---|---|
| 6,019,745 A | 2/2000 | Gray |
| 6,123,686 A | 9/2000 | Olsen et al. |
| 6,338,200 B1 | 1/2002 | Baxa et al. |
| RE38,189 E | 7/2003 | Walker et al. |
| D481,121 S | 10/2003 | Evans |
| D485,356 S | 1/2004 | Evans |
| 6,685,678 B2 | 2/2004 | Evans et al. |
| 6,790,198 B1 | 9/2004 | White et al. |
| 6,960,192 B1 | 11/2005 | Flaherty et al. |
| 7,074,209 B2 | 7/2006 | Evans et al. |
| 7,115,113 B2 | 10/2006 | Evans et al. |
| 7,117,041 B2 | 10/2006 | Engleson et al. |
| 7,161,488 B2 | 1/2007 | Frasch |
| 7,470,266 B2 | 12/2008 | Massengale et al. |
| 7,722,083 B2 | 5/2010 | McCarthy et al. |
| 7,727,196 B2 * | 6/2010 | Neer ............................ 604/154 |
| 7,834,816 B2 | 11/2010 | Marino et al. |
| 7,991,627 B2 | 8/2011 | Hutchinson et al. |
| 8,035,517 B2 | 10/2011 | Gibson |
| 8,133,178 B2 * | 3/2012 | Brauker et al. ............... 600/365 |
| 8,151,835 B2 | 4/2012 | Khan et al. |
| 2002/0040208 A1 * | 4/2002 | Flaherty et al. .......... 604/288.01 |
| 2002/0098598 A1 | 7/2002 | Coffen et al. |
| 2002/0099334 A1 | 7/2002 | Hanson et al. |
| 2002/0188259 A1 | 12/2002 | Hickle et al. |
| 2003/0012701 A1 | 1/2003 | Sangha et al. |
| 2003/0052787 A1 | 3/2003 | Zerhusen et al. |
| 2003/0055685 A1 | 3/2003 | Cobb et al. |
| 2003/0065537 A1 | 4/2003 | Evans |
| 2003/0088238 A1 * | 5/2003 | Poulsen et al. ............. 604/890.1 |
| 2003/0139701 A1 | 7/2003 | White et al. |
| 2003/0140929 A1 | 7/2003 | Wilkes et al. |
| 2003/0174326 A1 | 9/2003 | Rzasa et al. |
| 2004/0051368 A1 | 3/2004 | Caputo et al. |
| 2004/0082918 A1 | 4/2004 | Evans et al. |
| 2004/0186437 A1 | 9/2004 | Frenette et al. |
| 2004/0204673 A1 | 10/2004 | Flaherty |
| 2005/0101905 A1 * | 5/2005 | Merry ............................. 604/19 |
| 2005/0106225 A1 | 5/2005 | Massengale et al. |
| 2005/0182358 A1 | 8/2005 | Veit et al. |
| 2005/0277890 A1 | 12/2005 | Stewart et al. |
| 2006/0079767 A1 | 4/2006 | Gibbs et al. |
| 2006/0079843 A1 * | 4/2006 | Brooks et al. ................. 604/151 |
| 2006/0116639 A1 | 6/2006 | Russell |
| 2006/0122577 A1 * | 6/2006 | Poulsen et al. ............. 604/890.1 |
| 2006/0144942 A1 | 7/2006 | Evans et al. |
| 2006/0226089 A1 | 10/2006 | Robinson et al. |
| 2006/0229551 A1 | 10/2006 | Martinez et al. |
| 2006/0258985 A1 | 11/2006 | Russell |
| 2007/0043335 A1 | 2/2007 | Olsen et al. |
| 2007/0136218 A1 | 6/2007 | Bauer et al. |
| 2007/0166198 A1 | 7/2007 | Sangha et al. |
| 2007/0167919 A1 | 7/2007 | Nemoto et al. |
| 2007/0191787 A1 | 8/2007 | Lim et al. |
| 2007/0279625 A1 | 12/2007 | Rzasa et al. |
| 2007/0299421 A1 | 12/2007 | Gibson |
| 2008/0045930 A1 | 2/2008 | Makin et al. |
| 2008/0051937 A1 | 2/2008 | Khan et al. |
| 2008/0061153 A1 | 3/2008 | Hickle et al. |
| 2008/0125724 A1 | 5/2008 | Monroe |
| 2008/0191013 A1 | 8/2008 | Liberatore |
| 2008/0208042 A1 | 8/2008 | Ortenzi et al. |
| 2008/0234630 A1 * | 9/2008 | Iddan et al. ...................... 604/48 |
| 2008/0243088 A1 | 10/2008 | Evans |
| 2008/0294108 A1 * | 11/2008 | Briones et al. ................ 604/131 |
| 2009/0018494 A1 | 1/2009 | Nemoto et al. |
| 2009/0036846 A1 | 2/2009 | Dacquay et al. |
| 2009/0043253 A1 | 2/2009 | Podaima |
| 2009/0069714 A1 | 3/2009 | Eichmann et al. |
| 2009/0085768 A1 * | 4/2009 | Patel et al. ............... 340/870.05 |
| 2009/0149744 A1 * | 6/2009 | Nemoto et al. ............... 600/432 |
| 2009/0157008 A1 | 6/2009 | Vitral |
| 2009/0159654 A1 * | 6/2009 | Grimard ....................... 235/375 |
| 2009/0294521 A1 | 12/2009 | de La Huerga |
| 2010/0065643 A1 | 3/2010 | Leyvraz et al. |
| 2010/0152562 A1 | 6/2010 | Goodnow et al. |
| 2010/0153136 A1 | 6/2010 | Whittacre et al. |
| 2010/0174266 A1 | 7/2010 | Estes |
| 2010/0262002 A1 | 10/2010 | Martz |
| 2010/0280486 A1 | 11/2010 | Khair et al. |
| 2010/0305499 A1 | 12/2010 | Matsiev et al. |
| 2011/0060198 A1 | 3/2011 | Bennett et al. |
| 2011/0111794 A1 | 5/2011 | Bochenko et al. |
| 2011/0112473 A1 | 5/2011 | Bochenko et al. |
| 2011/0112474 A1 | 5/2011 | Bochenko et al. |
| 2011/0176490 A1 * | 7/2011 | Mehta et al. .................. 370/328 |
| 2011/0220713 A1 | 9/2011 | Cloninger |
| 2011/0224649 A1 | 9/2011 | Duane et al. |
| 2011/0264069 A1 | 10/2011 | Bochenko |
| 2012/0037266 A1 | 2/2012 | Bochenko |
| 2012/0041355 A1 * | 2/2012 | Edman et al. .................... 604/20 |

* cited by examiner

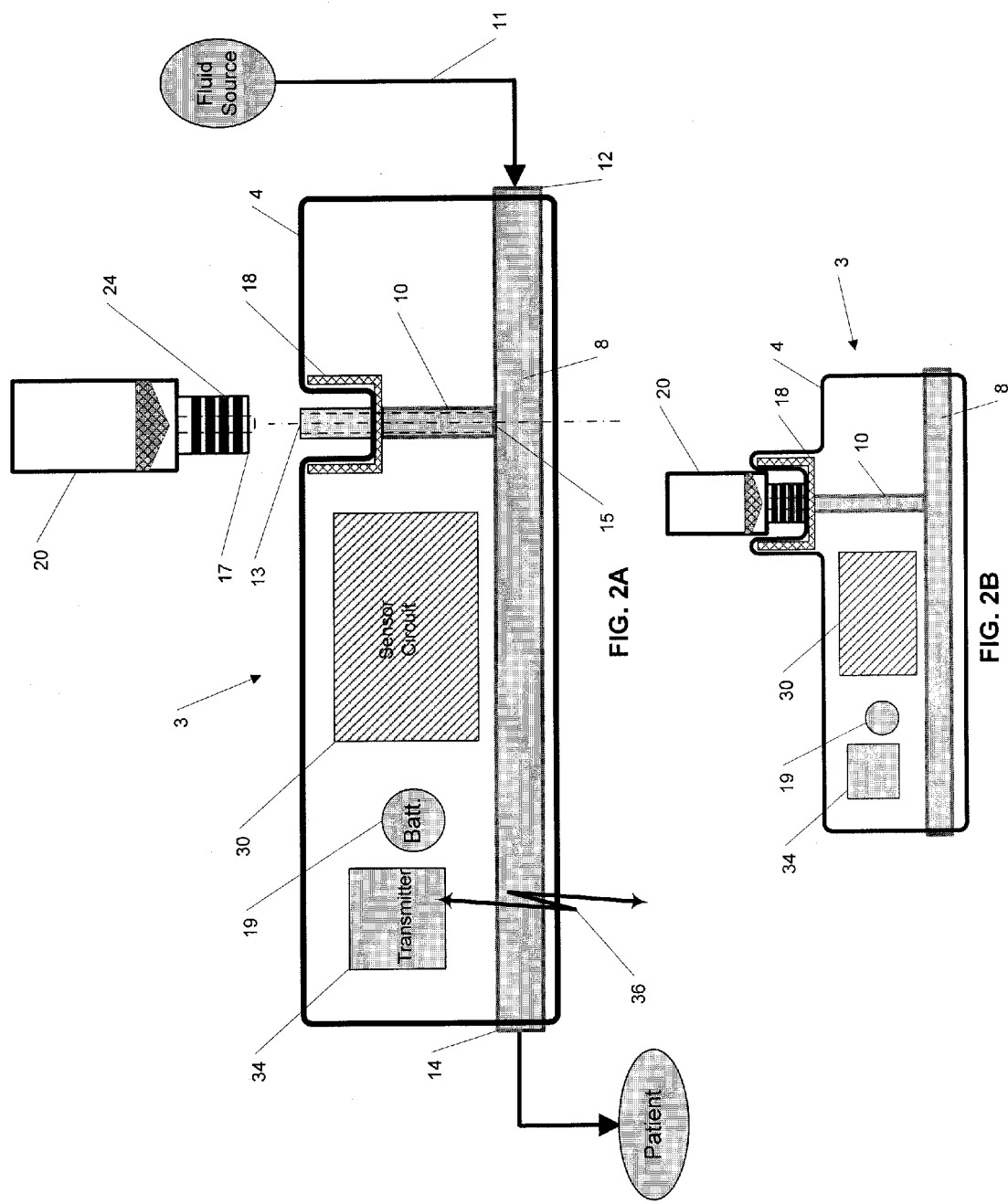

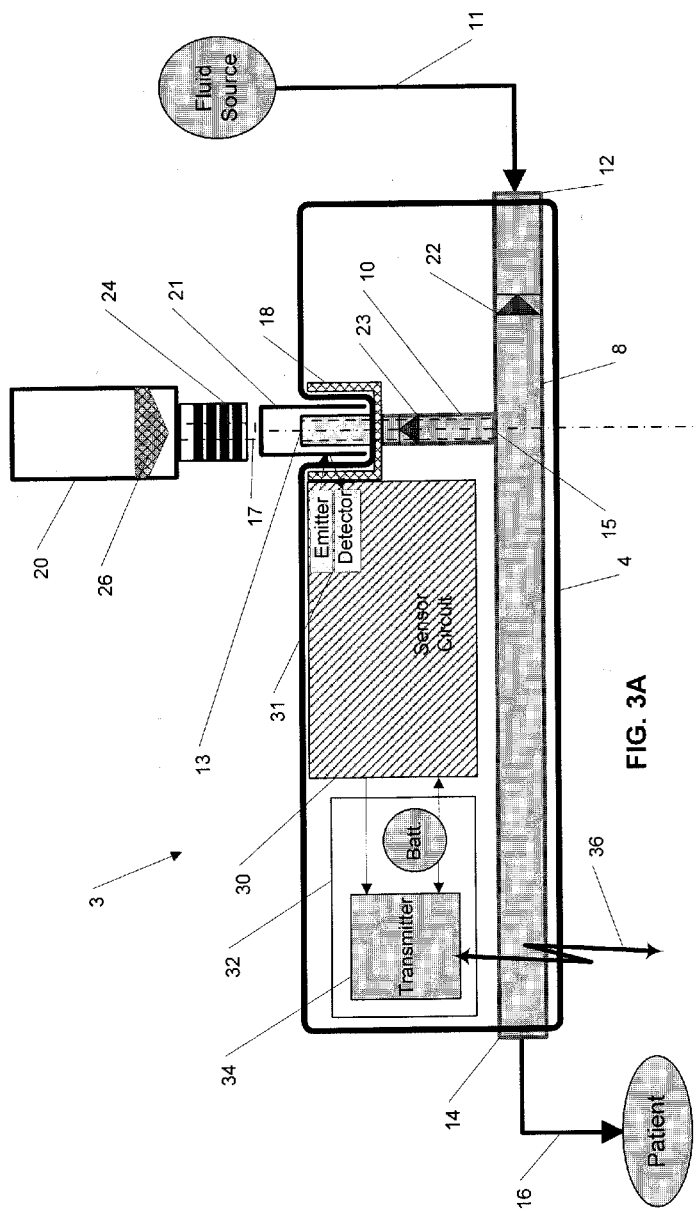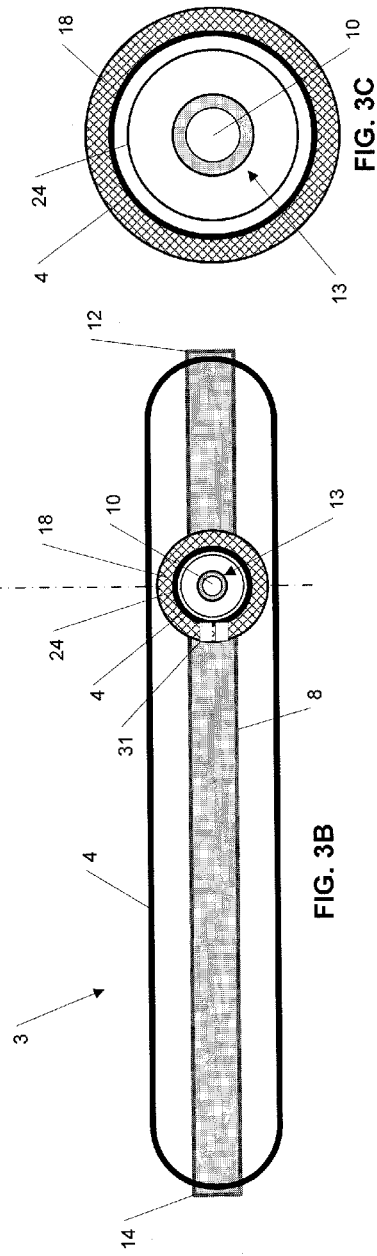
FIG. 3A
FIG. 3B
FIG. 3C

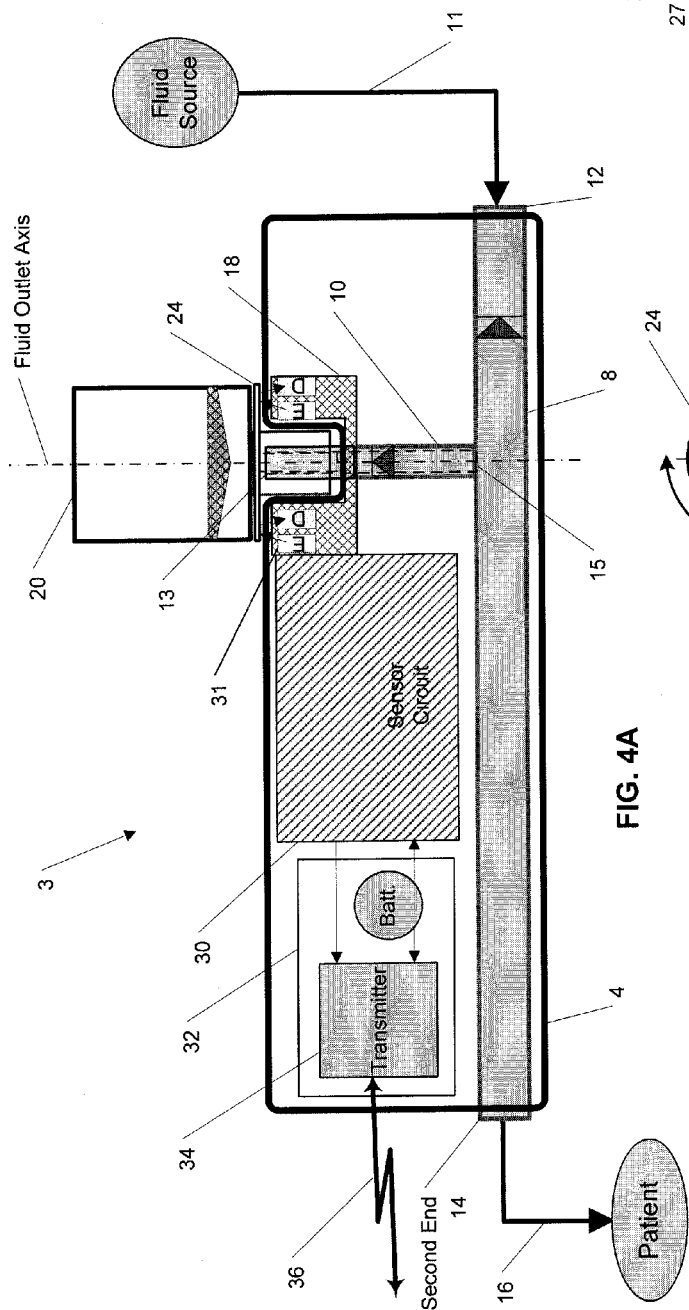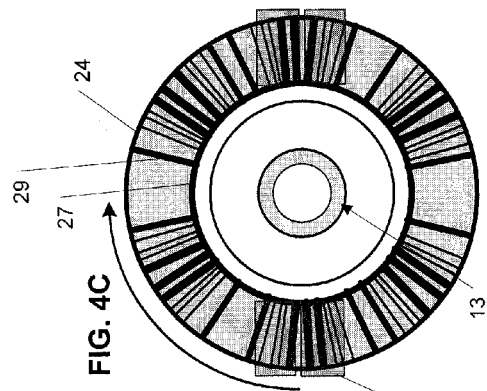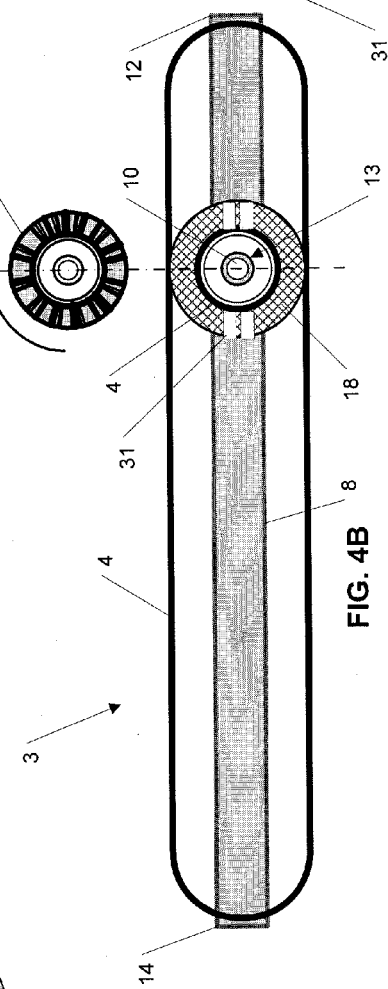

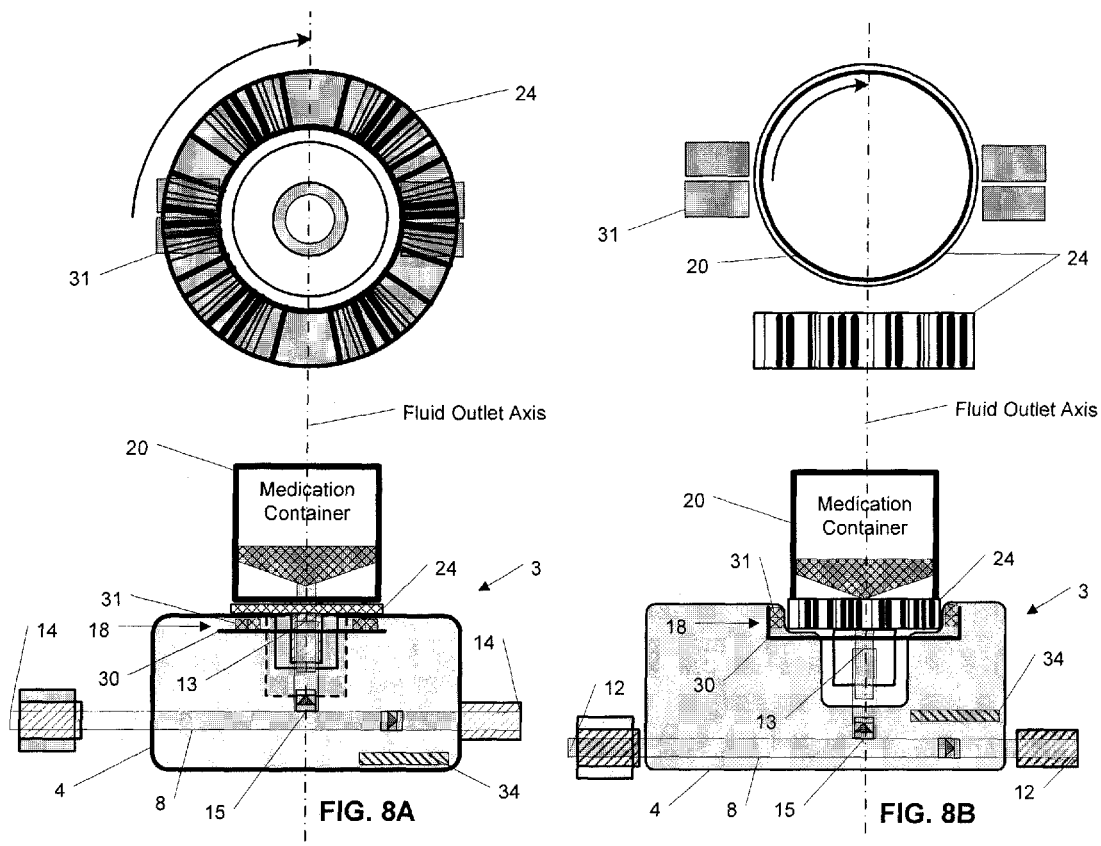
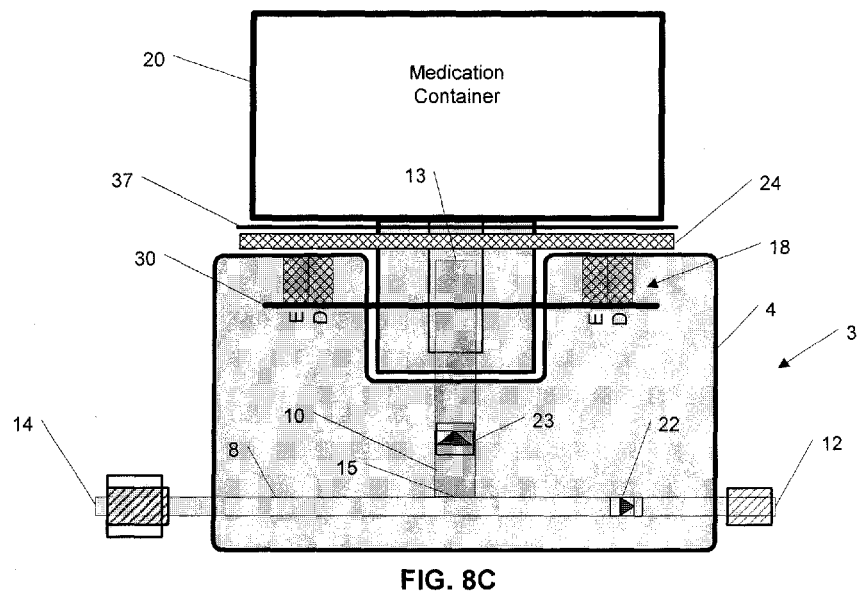

9A – Straight thru flow w/Side Port
9B - Right Angle flow w/Side Port
9C - "Y" Site w/Flow-thru Port Volume = Rate x Time
V = R x T Discharge Rate = R $R = C_S \times A2/A1 \sqrt{2g \times (p1-p2)}$ Cs = emperical system constant
g = density of fluid

MEDICATION INJECTION SITE AND DATA COLLECTION SYSTEM

RELATED APPLICATION

This application is a continuation-in-part of U.S. patent application Ser. No. 12/614,276 entitled "Medication Injection Site and Data Collection System" filed on Nov. 6, 2009, the contents of which are hereby fully incorporated by reference.

FIELD

The subject matter described herein relates to a medication injection site for intelligent delivery of medications into a fluid path for delivery to a patient as well as related data collection systems.

BACKGROUND

Many health care procedures involve a sequence of medication administrations to complete a specialized protocol. The type of medication and timing of administration are important to record in order to provide healthcare providers real-time information on the conduct of the procedure and the completion of a medical record. Some specialized protocols require quick medication administrations with limited time for documentation and record keeping.

SUMMARY

In one aspect, a medication site is provided that includes a housing, a junction element, a medication port, an identification sensor, a transmitter, and a self-container power source. The junction element can at least partially extend within the housing to form a first fluid channel and a second fluid channel. The first fluid channel extends from a first end to a second end. The second fluid channel extends from a distal end and terminates at the first fluid channel at an intersection intermediate the first end and the second end. The medication port is fluidically coupled to the distal end of the second fluid channel and is configured to be fluidically coupled to a fluid outlet of a medication container. The identification sensor is disposed within the housing to generate information indicative of contents of the medication container when the fluid outlet of the medication container is fluidically coupled to the medication port. The transmitter is disposed within the housing and in communication with the identification sensor to wirelessly transmit the information generated by the identification sensor to a remote data collection system. The term transmitter in this context can refer to a transmitter only or a transceiver, a combined transmitter-receiver (unless otherwise specified). The self-contained power source is disposed within the housing and it powers components within the medication injection site such as the identification sensor and the transmitter. In some implementations, the housing has a shape and size enabling it to be held by a first hand of a user while the user administers medication from the medication container via the medication port using his or her second hand.

A largest dimension of the housing can, in some implementations, be less than or equal to 10 centimeters. In addition or in the alternative, a weight of the system can be less than or equal to 500 grams, and in some implementations, 250 grams, and in other implementations less than or equal 100 grams.

The first end of the first fluid channel can be fluidically coupled to tubing extending to a fluid source. The fluid source can be suspended (e.g., IV drip bag, etc.) and fluid contained therein can be gravity fed via the tubing into the first channel. With such a variation, the housing can be suspended below the fluid source and supported by the tubing during use. The second end of the first fluid channel can be fluidically coupled to a patient. In other variations the housing can be located downstream more closely associated with the patient's catheter.

A self-contained fluid delivery sensor can be disposed within the housing and in communication with the transmitter to characterize fluid flow through one or more of the first fluid channel and the second fluid channel. With such arrangements, the transmitter can wirelessly transmit data characterizing fluid delivery to the remote data collection system. The fluid delivery sensor can measure fluid flow and/or pressure in the first fluid channel. Alternatively or in addition, the fluid delivery sensor measures fluid flow and/or pressure in the second fluid channel. The fluid delivery sensor can either be a pressure sensor, a differential pressure sensor or a fluid flow sensor.

The junction element can contain a diaphragm portion along one or more of the first fluid channel and the second fluid channel and the fluid delivery sensor can be positioned adjacent to the diaphragm.

The remote data collection system can calculate volume of fluid delivered via the medication port based on the wireless transmitted data characterizing fluid delivery.

A self-contained power source can be disposed within the housing to power one or more of the identification sensor, the fluid delivery sensor, and the transmitter.

An intersection of the first fluid channel and the second fluid channel can form a substantially T-shaped junction. In other variations, an intersection of the first fluid channel and the second fluid channel can form a substantially Y-shaped junction.

The medication port can define a cavity extending inwardly from an outer surface of the housing such that the fluid outlet of the medication container is substantially enveloped within the housing and does not extend beyond the outer surface when such fluid outlet is mechanically coupled to the port.

The medication container can bear an information source characterizing contents of the medication container. The information source can be, for example, mechanically encoded information, magnetically encoded information, and radio frequency readable information. The information source can also or alternatively comprise optically encoded information and the identification sensor can comprise an optical emitter and an optical detector to read the optically encoded information. The identification sensor can read information from the information source as a result of relative motion of the fluid outlet relative to the medication port. The identification sensor can read information from the information source in response to mechanically coupling the fluid outlet to the medication port.

The medication container can be a needle-less syringe, and the fluid outlet can be a tip of the syringe. The medication container can be a premixed solution provided in a bag, and the fluid outlet can be a luer fitting connector or an IV set spikeable port.

The junction element can be a unitary injection molded fitting.

Medication can be intermittently delivered through the medication port such that it is continuously or substantially continuously delivered to the first fluid channel via the first end of the first fluid channel.

A first check valve can be disposed within the first fluid channel intermediate the intersection and the first end of the first fluid channel to prevent fluid delivered into the medication port from exiting the first fluid channel at the first end. A second check valve can be disposed within the secondary fluid channel to prevent fluid entering the first fluid channel at the first end from exiting the secondary fluid channel at the distal end.

The housing can comprise a plurality of sections, and one or more of the first fluid channel and the second channel can be formed when at least two of the sections are assembled. At least two of the sections of the housing can be injection molded and one or more of the first fluid channel and the second fluid channel can be formed by one or more injection molded sections.

In one implementation, the medication injection site can be separated into two sub-housings, a reusable sub-housing, a disposable sub-housing that are coupled to each other via a connection interface. The reusable sub-housing can be used by one or more patients while the disposable sub-housing is intended to only be used by a single patient (i.e., the components contained within the disposable sub-housing provide a sterile fluid passageway which are separate from the components within the reusable sub-housing ensuring patient safety). The reusable sub-housing can contain elements of the medication injection site that are not part the first fluid channel or the second fluid channel (e.g., one or more of the identification sensor, the transmitter, a processor, a memory, etc.). The disposable sub-housing can contain the first fluid channel and the second fluid channel. The power source can be positioned in either sub-housing.

A removable sterility cap can be affixed to the medication port. Removal of the sterility cap can initiate communications between the transmitter and the remote data collection system.

A self-contained power source (e.g., battery, battery array, etc.) can be disposed within the housing powering one or more of the identification sensor, the fluid delivery sensor, and the transmitter. Removal of the sterility cap affixed to the medication port can initiate provision of electricity by the power source to the identification sensor and the transmitter.

The shape and size of the housing can enable positioning of the housing on arm of a patient adjacent to an injection site on the patient.

The medication port, can in some variations, be disposed wholly or at least substantially wholly within the housing. The medication port can additionally or alternatively be integrated into the junction element.

A memory element can be disposed within the housing that can store information obtained from the identification sensor and/or the fluid delivery sensor. A timing element can be coupled to the memory element to enable recordation of events corresponding to time of medication administration, duration of medication administration, and time of wireless transmission of information generated by the identification sensor. The remote data collection system can wirelessly request the transmitter to send information stored in the memory element obtained from the identification sensor. In addition, the remote data collection system can comprise a timing element to assign clock times to each data record based on absolute time and duration between recorded transmissions.

The system can include an identifier (e.g., serial number or alphanumeric identifier, bar code label, etc.) to uniquely identify wireless transmissions from the transmitter. The identifier can be encapsulated in some or all of the wireless transmissions, or it can be manually accessed or scanned by a practitioner.

The medication injection site can be enveloped in a sterile pouch (i.e., enclosure, etc.). The medication injection site can be part of a kit that also contains instructions for use.

In a first interrelated aspect, a medication injection site includes a housing, a junction element, a medication port, an identification sensor, a transmitter, and a self-container power source. The junction element at least partially extends within the housing forming a first fluid channel and a second fluid channel. The first fluid channel extends from a first end to a second end. The second fluid channel extends from a distal end and terminates at the first fluid channel at an intersection intermediate the first end and the second end. The medication port is fluidically coupled to the distal end of the second fluid channel and is can be configured to be fluidically coupled to a fluid outlet of a medication container. The identification sensor is disposed adjacent to the second fluid channel to generate information indicative of contents of the medication container when the fluid outlet of the medication container is fluidically coupled to the medication port. The transmitter is disposed within the housing and in communication with the identification sensor to wirelessly transmit the information generated by the identification sensor to a remote data collection system. A self-contained power source is disposed within the housing powering the identification sensor and the transmitter.

A self-contained fluid delivery sensor can be disposed within the housing and in communication with the transmitter to characterize fluid flow through one or more of the first fluid channel and the second fluid channel. With such a variation, the transmitter further can wirelessly transmit data characterizing fluid delivery to the remote data collection system.

In yet another interrelated aspect, a medication injection site includes a housing, a medication port extending from an outer surface of the housing, an identification sensor disposed within the housing to generate information indicative of contents of the medication container when the fluid outlet of the medication container is fluidically coupled to the medication port, a transmitter disposed within the housing and in communication with the identification sensor to wirelessly transmit the information generated by the identification sensor to a remote data collection system. The housing has a shape and size enabling it to be held by a first hand of a user while the user administers medication from the medication container via the medication port using his or her second hand.

In a further interrelated aspect, an apparatus to identify contents of a medication container is provided. Such a medication container includes a barrel portion, a fluid outlet tip, and a tapered portion intermediate the barrel portion and the fluid outlet tip. The apparatus includes an identification member having an opening larger than a diameter of the fluid outlet tip and smaller than or equal to the diameter of the barrel portion. In other variations the identification member can be slightly larger in diameter than the barrel portion. The identification member can contain optical, magnetic, and/or mechanically encoded information. The information can be indicative of one or more of the contents of the medication container, the volume of fluid within the medication container, and the expiration date of the contents of the medication container. The information can be readable by an identification sensor when the identification member is located around the fluid outlet tip and the apparatus is coupled to or adjacent to a fluid delivery system to deliver contents of the medication container.

In another aspect, a housing can include a reusable sub-housing and a disposable sub-housing. The reusable sub-housing can be operatively coupled to the disposable sub-housing. In addition, the reusable sub-housing is intended for use by a plurality of patients and the disposable sub-housing is intended for use by a single patient. Such an arrangement can also include a medication port configured to be fluidically coupled to a fluid outlet of a medication container, an identification sensor disposed within the housing to generate information indicative of contents of the medication container when the fluid outlet of the medication container is fluidically coupled to the medication port, a transmitter disposed within the housing and in communication with the identification sensor to wirelessly transmit the information generated by the identification sensor to a remote data collection system, and a power source disposed within the housing powering the identification sensor and the transmitter.

In one implementation, the medication port is within the disposable sub-housing and one or more of the identification sensor, the transmitter, and the power source are in the reusable sub-housing.

The identification member can be disposed radially about a central fluid outlet axis of the fluid outlet tip enabling detection of the information when the medication container is rotated about the central fluid outlet axis.

The information can be disposed linearly enabling detection of the information when the medication container is joined with a fluid pathway along a central fluid outlet axis of the medication container. The information can be selected from a group comprising: optically encoded information, magnetically encoded information, radio frequency detectable information, and mechanically detectable information.

The medication container can be a first medication container and the identification member can be releasably secured to the medication container to allow it to be removed for placement on a second medication container. The identification member can bear an attachment element allowing it to be removed from the first medication container and affixed to the second medication container. Transfer of the identification member from the first medication container to the second medication container can be completed during the process of transferring the medication from the first medication container to the second medication container.

The identification member can be a label adhered to the medication container. The identification member can be integral to the medication container. The identification member can be a ring shaped member configured to fit around the fluid outlet tip.

In another aspect, a system can include a housing, a medication port, a transmitter, and a power source. The medication port is configured to be fluidically coupled to a fluid outlet of a medication container. The identification sensor generates information indicative of contents of the medication container when the fluid outlet of the medication container is fluidically coupled to the medication port. The transmitter is in communication with the identification sensor to wirelessly transmit the information generated by the identification sensor to a remote data collection system. The remote data collection system is coupled to or integral with a secondary medical device. The power source can power the identification sensor and the transmitter.

The secondary medical device can be, for example, a physiological sensor, a defibrillator, an infusion pump, a ventilator, an anesthesia machine. Example physiological sensors include an EKG monitor, a blood pressure monitor, an ETCO2 monitor, a pulse oximeter.

The data collection system can receive information from a medication injection site and or a secondary medical device. The data collection system can be coupled to or form part of a cellular phone or other mobile computing system (e.g., tablet computer, IPAD, etc.).

The subject matter described herein provides many advantages. For example, the current subject matter allows for compact fluid injection port systems that automatically identify administered medication and/or determine volume of administered medication. The fluid injection port is sufficiently small to be placed on a standard IV line (and to be self-supporting) allowing it to be used in multiple situations including on-site paramedic treatments, during ambulance delivery of patients, as well as medical facilities such as emergency rooms/operating rooms. Moreover, as medical staff (e.g., doctors, nurses, etc.) are accustomed to delivering medicine through Y-sites on IV lines, the current subject matter requires little, if any, behavior modifications while allowing for intelligent delivery of medication and logging of administered medications. In addition, the compact nature of the fluid injection port obviates the need for a larger tabletop or cradle unit which can be cumbersome during code blue or other emergency events and which can require much needed space (displacing other required equipment). Furthermore, the current subject matter eliminates manual record keeping and other activities that can tend to detract from the needed attention to a patient. Automated record keeping frees up the health care provider's time enabling improved patient care. Lastly, the current subject matter is advantageous in that the medication injection site can be disposable (thereby increasing patient safety).

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings:

FIG. 2A is a diagram illustrating a first variation of a medication injection site with a medication port flush with or disposed within a cavity of a housing;

FIG. 2B is a diagram illustrating a second variation of a medication injection site with a medication port extending outside a housing;

FIG. 3A is diagram illustrating a detailed view of a medication injection site as in FIG. 2A;

FIG. 3B is a diagram illustrating a side view of a medication injection site as in FIG. 3A;

FIG. 3C is a diagram illustrating a magnified cross-sectional view of elements in FIG. 3B;

FIG. 4A is a diagram illustrating a medication injection site with a medication container bearing an alternate information source to that of FIG. 3A;

FIG. 4B is a diagram illustrating a side view of a medication injection site as in FIG. 4A;

FIG. 4C is a diagram illustrating a magnified view of a medication container having an alternate information source as in FIGS. 4A and 4B;

FIG. 8A is a diagram illustrating a medication container having a radial information source as in FIG. 4A in greater detail;

FIG. 8B is a diagram illustrating an alternate location for a radial information source;

FIG. 8C depicts a magnified view of elements shown in FIG. 8A;

Like reference symbols in the various drawings indicate like or similar elements.

DETAILED DESCRIPTION

Figure 1:
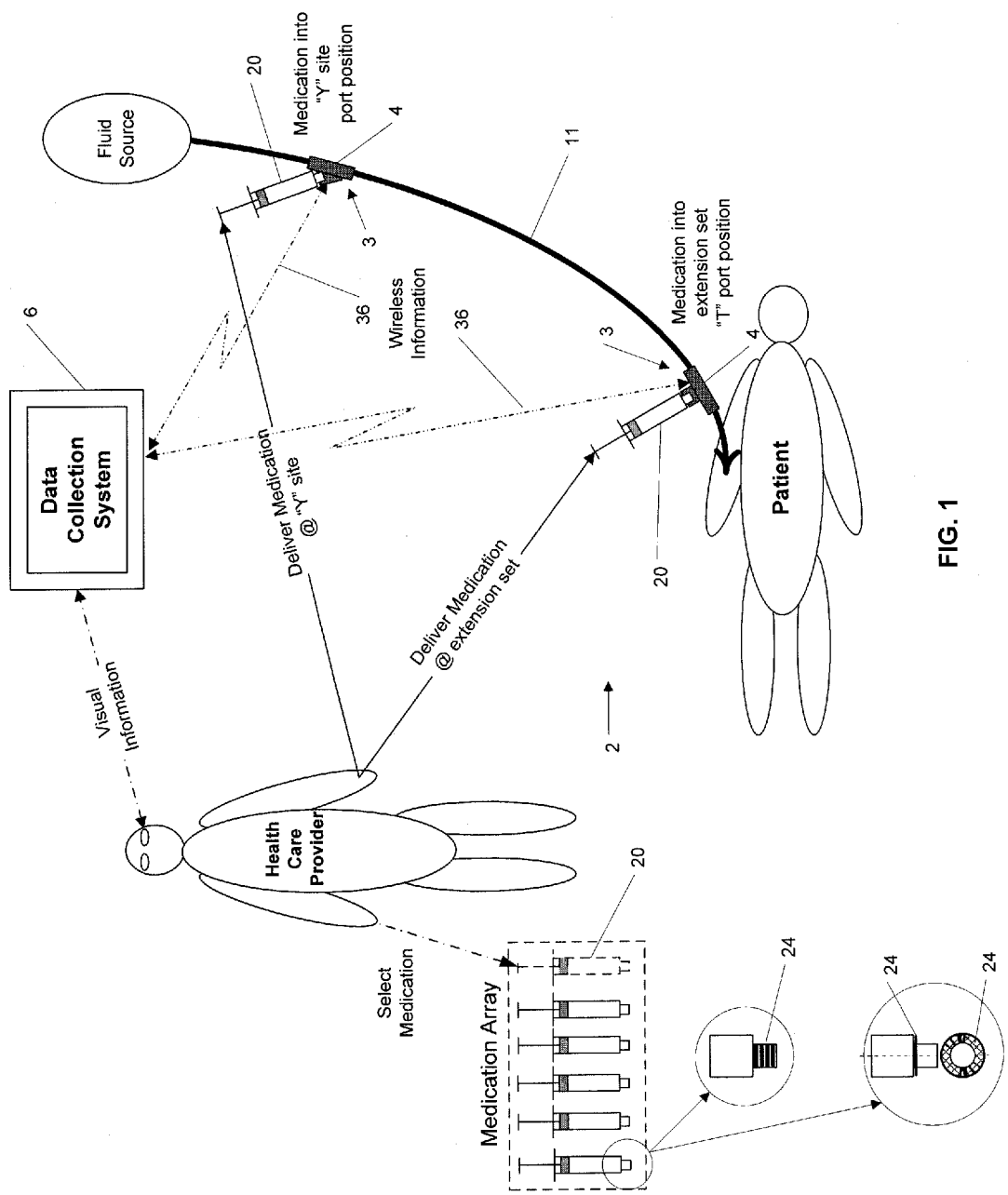
FIG. 1 is a diagram illustrating a healthcare provider using a medication injection site in connection with the care of a patient.

FIG. 1 is a diagram illustrating a system 2 in which a healthcare provider oversees the care of a patient. In particular, the healthcare provider selects and administers medications from an array of available medications. A medication container 20 can carry an information source 24 that provides detectable information indicative of the medication in the container and/or of the volume of the contents of the container. After selecting the appropriate medication, the healthcare provider delivers it to medication injection site 3 located on tubing set 11 connected to the patient. As shown in FIG. 1, the medication injection site 3 can be positioned at different locations along tubing set 11. In some implementations, the location can be close to the fluid source bag (e.g., saline bag, etc.) where the medication injection site 3 is affixed to or acts as a "Y" site on the tubing set 11. Alternately, medication injection site 3 can be in the form of an extension set located lower on tubing set 11 closer to the patient's infusion site. In either location, a sensor at least partially enclosed by housing 4 of medication injection site 3 can detect the presence and type of medication container 20 and transmit information 36 via wireless communications to data collection system 6. Medication injections (from one or more medication containers 20) can be time stamped and recorded in a history log and/or added to the patient's medical records and/or billing records. The healthcare provider can view on a display of data collection system 6 which medication has been injected into the patient and when such medication was administered. Immediate display of information assists the healthcare provider in making further medication decisions for the care of the patient.

FIGS. 2A and 2B are diagrams illustrating medication injection site 3 with medication container 20 in a spatially separated state (FIG. 2A) and a coupled state (FIG. 2B). In this variation, the medication injection site 3 can include a first fluid channel 8 and a second fluid channel 10 (other channels may be included in some implementations). The first and second fluid channels 8, 10 may be fully enclosed by the housing 4 or one or both may extend outwards from the housing (e.g., if the fluid channels 8, 10 comprise flexible tubing with connection adapters for coupling to further tubing). The first and second fluid channels 8, 10 are sometimes collectively referred to herein as a fluid junction element. In some variations, the fluid junction element can comprise a unitary element (e.g., injection molded material, etc.). With other variations, the fluid junction element can comprise a plurality of sections (i.e., it is non-unitary) and/or is integrated with the housing (e.g., sections of the housing form the fluid paths).

The first fluid channel 8 can extend from a first end 12 to a second end 14. The second fluid channel 10 can extend from an opening of medication port 13 at a distal end and can terminate at the first fluid channel 8 at intersection 15 intermediate the first end 12 and second end 14. The medication port 13 can be configured to fluidically couple to a fluid outlet 17 of medication container 20.

An identification sensor 18 can be at least partially disposed within housing 4 (i.e., the identification sensor 18 can be enclosed by the housing 4 or a portion of it can extend outwards from an outer surface of the housing 4, etc.) to generate information indicative of contents and/or volume of contents of medication container 20. In some variations, the identification sensor 18 can generate such information when fluid outlet 17 of medication container 20 is fluidically coupled to medication port 13. In other variations, the identification sensor can generate such information when fluid outlet 17 of medication container is adjacent to medication port 13. A transmitter 34 can be disposed within housing 4 and in communication with/coupled to identification sensor 18 to wirelessly transmit the information 36 generated by the identification sensor 18 to the remote data collection system 6. Examples of wireless transmission hardware and protocols can be utilized such as Bluetooth, Zigbee, Continue, Wireless USB, Wibree, IEEE 802 relevant standards (e.g., 802.11, 802.15, or 802.16, etc.) and other methods. The data transmissions can, in some implementations, be encrypted in order to ensure patient privacy and/or to comply with various laws relating to handling of medical data. The transmitter 34 can have such encryption capabilities or one or more additional chipsets can be incorporated within the medication injection site 3 to provide such encryption. The signal from identification sensor 18 can be processed and readied for transmission by sensor circuit 30. A self-contained power source 19 (e.g., battery or battery array, etc.) can be disposed within housing 4 to provide power for one or more of identification sensor 18, sensor circuit 30 and transmitter 34.

Housing 4 and/or the entire medication injection site 3 can have a shape and size enabling it to be hand-held by a first hand of a user while the user administers medication from medication container 20 via the fluid outlet 17 using his or her second hand. The housing 4 and/or the entire medication injection site 3, excluding any external tubing can, in some implementations have a largest dimension of 10 centimeters or less. In addition, the entire housing 4 and its contained components and/or the entire medication injection site 3 can be lightweight being less than 1 kg, and in some implementations, less than 500 grams. The compact and/or lightweight nature of the medication injection site 3 allow it to be suspended below the fluid source at a Y-site (or to replace a Y-site) and supported by the tubing set 11 during use (see diagram of FIG. 10B). Alternately, the small size and weight can facilitate use on tubing set 11 closer to a patient's injection site and can be conveniently secured to the patient's arm.

In some implementations, housing 4 can be separated into two sub-housings (see diagrams in FIGS. 15A, 15B, 15C). A reusable sub-housing 80 can house reusable elements (i.e., elements that can be safely used among several patients, etc.) while a disposable sub-housing 82 can house disposable elements (i.e., low-cost and/or sterile elements that are recommended for use in connection with a single patient, etc.). The sub-housings can be operatively coupled by connecting element 84 thus forming a fully functional injection site 3.

Housing 4 can be made of a rigid material that protects the component contained within the housing 4 from handling and fluids during use. Housing 4 can rigidly position and fix its contained components relative to each other. Housing 4 can be made by plastic injection molding a material such as polystyrene or polycarbonate to form one or more pieces of the housing. Sections of the housing 4, can in some implementations, form the first fluid channel 8 and the second fluid channel 10. In one variation, the entire housing 4, including the medication port 13, the first and second channels 8, 10 and internal components can be provided sterile with protective sterility covers on the first end 12 and the second end 14 of first fluid channel 8 as well as medication port 13.

All or some of the components of the medication injection site 3 can be selected so as to withstand conventional single use medical device sterilization processes such as EtO or radiation. The medication injection site 3 can be packaged with sterility covers in place in a peel-pouch kit configuration and provided to the user with a sterile fluid delivery pathway ready for use with sterile medications and/or fluids. Instruction for use and/or other identifying materials may be included with the medication injection site 3 to form a kit.

Removal of one or more of the sterility covers on medication injection site 3 can result in the self-contained power source 19 powering one or more of the transmitter 34 and the sensor circuit 30. Initial power-up sequences can synchronize communications between transmitter 34 and receiver 42 (see FIG. 5). Indicator 35 (see FIG. 5) can indicate readiness for medication delivery and data collection system 6 can indicate the start of medication record keeping.

FIGS. 3A-C depict various features of the medication injection site 3. With reference to FIG. 3A, the first end 12 of first fluid channel 8 can be attached to a fluid source through tubing set 11 and the second end of first fluid channel 8 can be attached to a patient through tubing set 16. While tubing sets 11 and 16 are illustrated as being separate, some variations include a single tubing set extending through the housing 4. First fluid channel 8 can join first end 12 (i.e., fluid inlet) and second end 14 (i.e., fluid outlet) forming a fluid path inside housing 4. First fluid channel 8 can be joined by second fluid channel 10 at intersection 15 for the administration of medication from container 20. Intersection 15 can be positioned such that the relationship between the first fluid channel 8 and the second fluid channel 10 is a right angle as shown in FIG. 3A substantially forming a "T"-shape. Alternatively, the channels 8, 10 can be positioned to form an acute angle. In some implementations, the angle is such that the first fluid channel 8 and the second fluid channel 10 form a "Y" shape.

A check valve 22 can be situated in the first fluid channel 8 upstream of intersection 15 to prevent fluid backflow upstream into the fluid source when the medication container 20 is delivering fluid into medication port 13. The second fluid channel 10 can contain a check valve 23 to prevent fluid flow from the first fluid channel 8 from flowing into the second fluid channel 10.

Medication container 20 can be a syringe or other medication container with compatible fluid coupling of outlet 17 on medication container 20 to medication port 13 (e.g., a slip luer, luer-lock fitting, etc.). Medication container 20 can include information source 24 located on the fluid outlet attachment tip of container 20. Such information source 24 can, in some implementations be affixed, integrated, secured, and/or adhered to a portion intermediate the fluid outlet of medication container 20 and a barrel portion of container 20. Such intermediate portion can be tapered and/or planar. The information source 24 can be an integrated feature of the medication container 20 such as etched or molded features. The information source 24 can alternatively be adhered to the fluid outlet attachment tip of medication container 20 (i.e., information source 24 can be a label, etc.). In addition, the information source 24 can be a separate element that extends around the fluid outlet of the medication container 20 (either during manufacture of the medication container or subsequently whether during distribution or use).

When provided to a user, medication port 13 can be protected by port cover 21. Prior to use, the port cover 21 maintains medication port 13 in a sterile condition. Similarly, when provided as an extension set (i.e., medication injection site 3 includes added tubing that increases functional capability of fluid administration line and extends the fluid tubing set 11), sterility covers can be provided on the first end 12 and the second end 14 of the first channel 8. When used, the medication injection site 3 can be connected to the fluid source by removing the sterility cover on the first end 12 and attaching tubing set 11. Secondly, the sterility cover can be removed from the second end 14, fluid flow is then established through first fluid channel 8 and then second end 14 is connected to tubing 16. Tubing 16 can then be attached to a patient's catheter for delivery of fluids and medications.

The identification sensor 18 can include an optical emitter/detector pair 31 with horizontal orientation on sensor 18 that detects encoded information contained on information source 24 (a sleeve around the fluid outlet of the medication container 20) parallel to the fluid outlet axis. The identification sensor 18 can comprise a plurality of sensors to detect information source 24. In some variations, the identification sensors can be sensors such as magnetic, mechanical, conductive, switchable RFID and/or proximity sensors. Sensor circuit 30 provides signal processing and connects identification sensor 18 to transmitter 34. The identification sensor 18 can be directly coupled to power source 19.

FIG. 3B depicts a side view of medication injection site 3. Housing 4 is sized and shaped to easily fit into a user's hand. The location of medication port 13 can be anywhere along the length of first channel 8 and conveniently positioned for ease of use.

FIG. 3C is an enlarged view of medication port 13 showing identification sensor 18 having a concentric (or at least partially concentric) configuration so that it can surround information source 24 on the outlet 17 of medication container 20. When medication container 20 is coupled to the medication injection site 3, outlet 17 is fluidically coupled to medication port 13 and information source 24 is simultaneously positioned for detection within and in close proximity to identification sensor 18.

FIGS. 4A, 4B and 4C depict an alternate implementation of information source 24 and identification sensor 18. FIG. 4A depicts a cross-sectional view of medication container 20 coupled to a medication injection site 3. The medication injection site 3 can include an optical emitter and detector pair 31 positioned and configured to optically detect encoded information on information source 24. Information source 24 can take the form of a disk or other element with an opening mounted over the fluid outlet perpendicular to the fluid outlet axis. Information source 24, when taking the shape of a disk, can be substantially planar and include an inner opening 27 (see, e.g., FIGS. 4A, 4C) that corresponds to fluid outlet 17 of medication container 20. Such an information source 24 can be mounted to medication container 20 so that inner hole 27 is concentric with fluid outlet 17 (and positioned so that medication container 20 can still be coupled to medication injection site 3 and medication can be delivered).

When used, information source 24 and medication container 20 can be rotated together clockwise to complete the fluid coupling of fluid outlet 17 to medication port 13. Barcode indicia 29 are also corresponding rotated. The optical emitter/detector pair 31 can scan (i.e., illuminate and detect) the rotated barcode indicia 29 and extract the identifying information. Such identifying information can then be passed from sensor circuit 30 to transmitter 34 for transmission.

In some implementations, the identification sensor 18 can include a series of more than one sensor to detect information source 24. In addition, the identification sensors can be other types of sensors such as magnetic, mechanical, conductive, switchable RFID and/or proximity sensors. With non-optical arrangements, the corresponding information source 24 and the detector 31 would be correspondingly modified. For example, if information source 24 comprises a magnetic strip, detector can be a magnetic strip reader. In addition, sensor circuit 30 provides signal processing and connects identification sensor 18 to transmitter 34.

Figure 5:
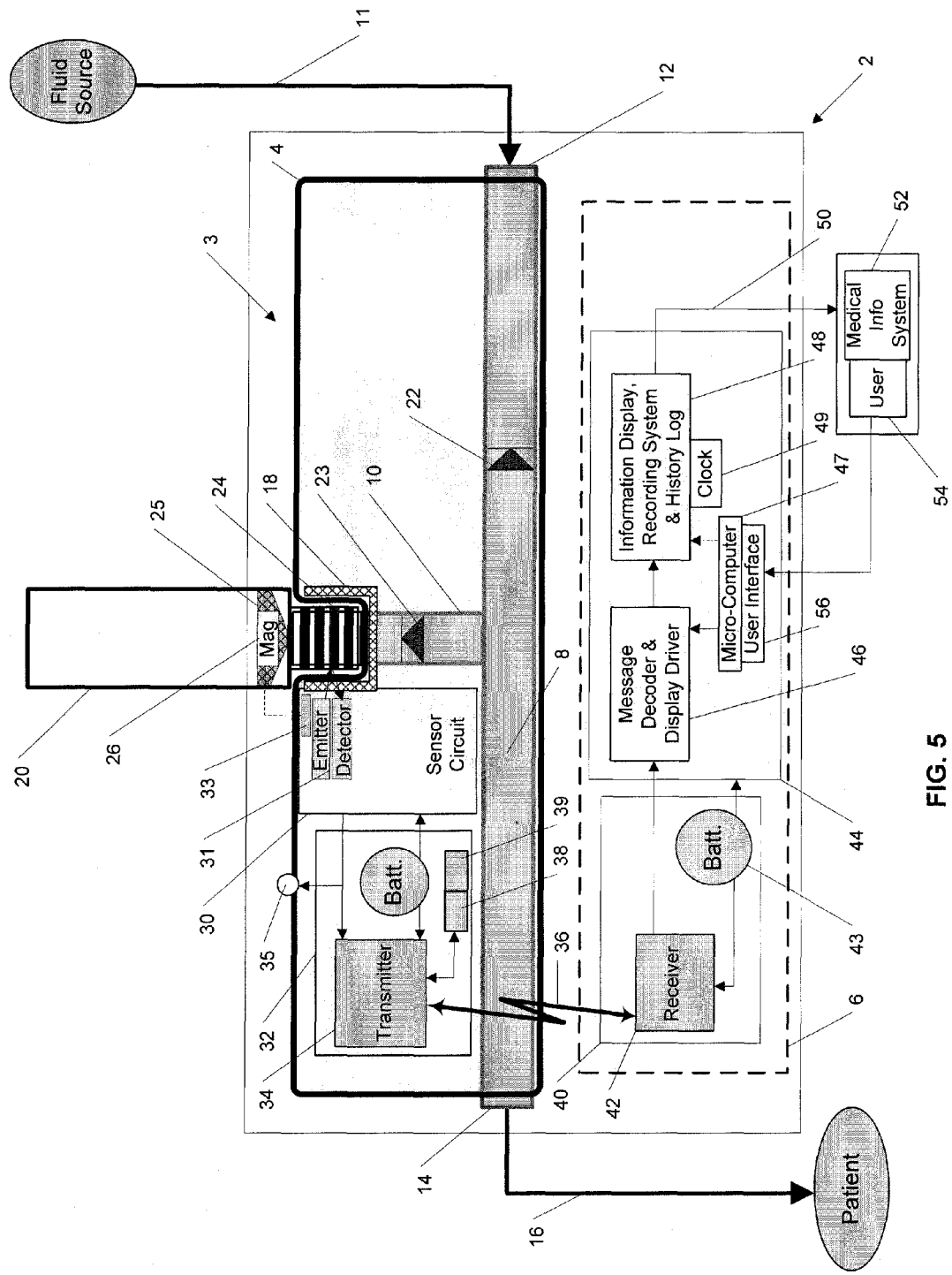
FIG. 5 is a diagram illustrating a medication injection site and a data collection system.

FIG. 5 depicts additional elements of system 2 including a medication injection site 3 with a centrally located second fluid channel 10, further elements contained within data collection system 6 and connection to a medical information system 52. Medication injection site 3 can include information processing and transmission circuit 32. Signals from sensor circuit 30 can be processed for transmission to data collection system 6 by circuit 32. Sensing circuit 30 can generate one or more signals in response to connection of medication container 20 to medication port 13. When identification sensor 18 detects connection of medication container 20 a visual and/or audible indicator 35 can be actuated to provide feedback to the user of proper connection. Transmitter 34 can transmit information 36 to receiver 42 contained in data collection system 6. When transmitter 34 transmits information 36 to receiver 42 a visual and/or audible indicator 35 can be actuated to provide feedback to the user of proper transmission.

The sensor circuit 30 can contain a Hall Effect sensor 33 that detects the completion of medication administration when magnetic indicator 26 is in close proximity to sensor 33. Alternatively, sensor 33 and indicator 26 can be optical, mechanical, conductive and/or or proximity sensor/detector pairs and provide a medication administration complete signal to circuit 32. In this case, a second information transmission 36 can be sent to receiver 42 in response to a signal from sensor 33. When transmitter 34 transmits information 36 to receiver 42 a visual and/or audible indicator 35 can be actuated to provide feedback to the user of proper transmission of the completion of medication administration.

Medication delivered from medication container 20 can flow via outlet 17 into the second fluid channel 10, past check valve 23 and into first fluid channel 8. Fluid from the fluid source enters first fluid channel 8 at first end 12, flows past check valve 22 and out to the patient through second end 14 and tubing 16.

Data collection system 6 receives information 36 (e.g., packetized data, etc.) from transmitter 34 within the medication injection site 3. In one variation, data collection system 6 can include a personal computer (see FIG. 14A). In another variation, the data collection system 6 can be small, light weight and configured to be stand-alone with a self-contained power source 43 (see FIG. 14B). The data collection system 6 can portable so that it can, for example, provide medication administration information for emergency medical services personnel in the field or it can used on mobile crash carts by health care providers within a hospital facility. In one implementation, after medications are delivered (or during delivery) and the health care protocol is complete data collection system 6 can be connected (e.g., via a web service, direct connection, etc.) to medical information system 52 for records transfer and/or data storage and/or patient billing, etc.

The data collection system 6 and/or the medication injection site 3 can initiate wireless exchange of information. Appropriate discovery/handshaking message exchanges are used to initiate communications (whether when the medication injection site 3 is first used or when there is an interruption of communications, etc.). The medication injection site 3 can interface with multiple data collection systems 6 at one time or simply pass information from a first data collection system 6 to subsequent data collection systems 6 (using, for example, memory resident in the medication injection site 3 as described below).

Within data collection system 6, information received by receiver 42 is sent to and processed by circuit 44. Circuit 44 contains a message decoder and display driver circuit 46, a micro-computer 47, an information display and recording system 48 and clock 49. Information received is time stamped by clock 49, logged into memory and displayed by circuit 48. Information displayed and recorded can include one or more of: the type and amount of medication delivered, time of medication administration, sequence of medications delivered, prompting messages providing real-time feedback to the healthcare provider on prior medications delivered, prompting messages for future medications to be administered with proposed protocol administration times, time since the medication was administered and other instructive information for conducting the health care protocol.

Display and recording system 48 can receive messages and generate a record documenting the time sequence of medication injections based upon signals received from sensor circuit 30. Display and recording system 48 can, in some variations, include a report generator capable of sending report information 50 to a medical information system 52. A user 54 can interact with micro-controller 47 via user interface 56 to provide additional information to the display and recording system 48. Additionally, user 54 can edit the report, add non-medication administration information to the report and complete filing of the report to a medical information system 52. Medical information system 52 may be coupled to a local network and/or accessible via the Internet.

Display and recording system 48 can take the received information 36 and combine it with time information from clock 49 to generate a time stamped information log. Computer system 47 can receive the time stamped information for each medication injection. The medication information included in the time stamped log file can include, but is not limited to, type of medication, volume of medication injected, expiration date of the medication, medication manufacturer's information and user edited report information. Such information can be integrated with medical files for the patient and/or submitted to a patient billing system (e.g., by web service, etc.).

The message decoder and display driver circuit 46 can convert each signal into an encoded value indicative of the medication administration. The encoded value can then be provided to computer system 47 that decodes the value and provides the user with understandable information about the injections for editing.

In some implementations, the medication injection site 3 can contain memory 38 to store medication administration data. The data can include a sequential record of each medication administration made through medication injection site 3. Timer 39 provides time count data to memory 38 separating each successive medication administration data element. Situations that can occur necessitating the use of memory 38 and timer 39 include: failure of data collection system 6, inadvertent user failure to activate data collection system 6, transfer of a patient from one data collection system 6 to another during transfer of the patient to different health care providers (field emergency medical service care provider to ambulance care provider to hospital emergency room care provider, etc.). In these situations the patient's medication administration data is stored in memory 38 and can be recalled later by a different data collection system 6. The memory 38, in some implementations, can be removable allowing it to be accessed by a computing system. For example, the memory 38 can be part of a USB card allowing it to be removed and accessed by a separate computing system. In some variations, the memory 38 can store software to either launch a local application on such separate computing system or to launch a particular web site or initiate a web service. In either of such scenarios, the patient data can be transported for storage and/or display on such separate computing system (or to another computing system remote from such separate computing system).

Various types of medication containers 20 can be used with the medication injection site 3, provided, that the fluid outlet 17 of the medication container can couple to the medication port 13. FIGS. 6A-8C illustrate various arrangements.

Figure 6A:
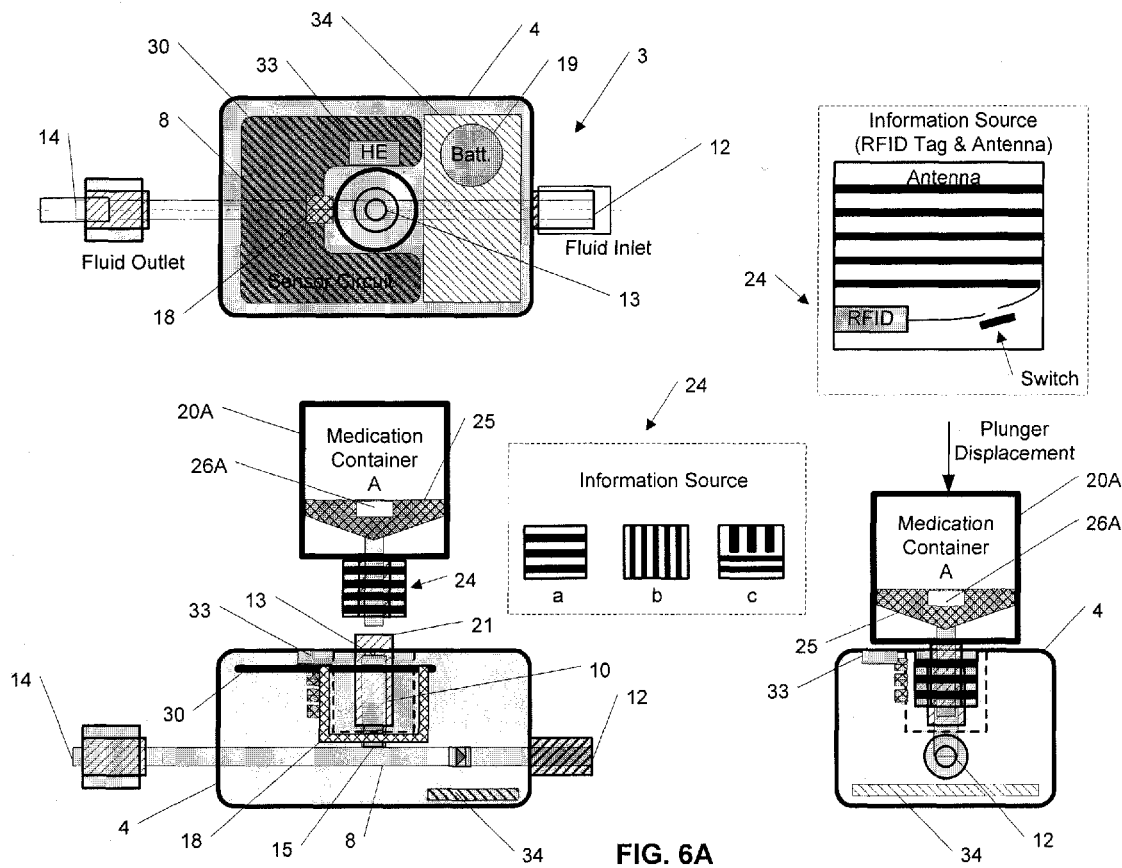
FIG. 6A is diagram illustrating a medication container containing an information source that can be optically detected.
Figure 6B:
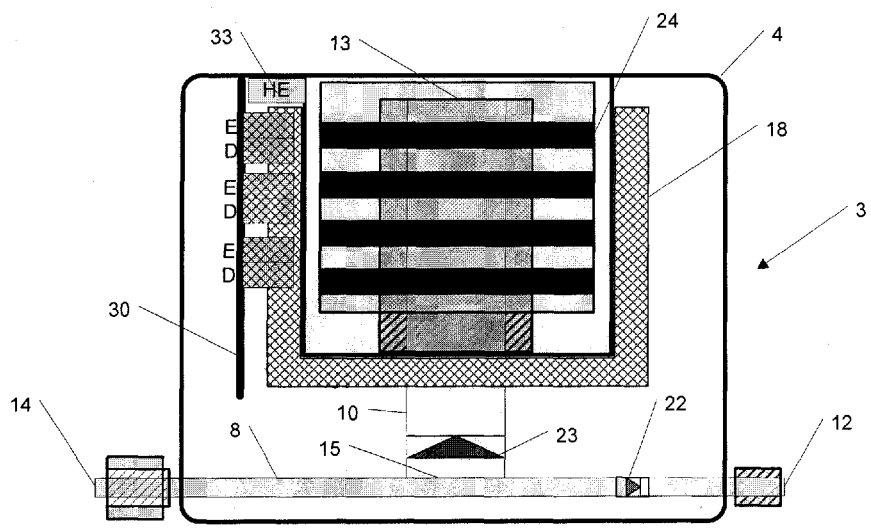
FIG. 6B is a diagram illustrating a magnified view of elements shown in FIG. 6A.

FIGS. 6A and 6B depict a medication injection site 3 with some elements removed for illustration purposes. FIG. 6A illustrates top and front views of housing 4 to the left with medication container 20A about to be coupled to medication port 13. A side view is depicted on the lower right with medication container 20A fully engaged with medication port 13. Fluid inlet first end 12 and fluid outlet second end 14 can be connected by first fluid channel 8. Fluid inlet 12 and fluid outlet 14 can be a slip luer, luer-lock or other fluid delivery fitting connectors and are typically fitted with sterile protective caps prior to use. Second fluid channel 10 can join first fluid channel 8 at intersection 15 Medication port 13 is initially provided for use with a sterile barrier cap 21 which is removed immediately prior to medication injection. Alternately, medication port 13 can be a swab-able needleless injection connector facilitating a luer connection from a syringe or other medication container 20. In some variations, the medication container 20 can include a needle which acts as the outlet 17 which in turn is fluidically coupled to the medication port 13.

The housing 4 can at least partially enclose identification sensor 18, sensor circuit 30, transmitter 34 and a common power source 19 (battery, battery array, etc.). Sensor circuit 30 can provide for one or more identification sensors 18 to detect information from medication information source 24. Transmitter 34 can process the sensor signals and transmits them to a data collection system 6.

In FIG. 6A medication container 20A can be a syringe with a fixed medication container and a slidable plunger 25 which moves during medication administration. Medication container (A) 20A can have a medication information source 24 affixed on the tip. There can be a number of variations (a, b, c) for information source 24. Information source 24a can contain information (e.g., readable data, etc.) indicative of the medication in one or more horizontal bands. Information source 24b contains information indicative of the medication in one or more vertical bands. Information source 24c contains information indicative of the medication in a combination of one or more horizontal and vertical bands.

Additionally, plunger 25 can contain a ferric material 26A that can be detected by a magnetic sensor 33. The ferric material 26A can be a magnet or other type iron material matched with ferric material type sensor 33. When the medication delivery is completed plunger 25 with ferric material 26A comes into close proximity with sensor 33 and a medication administration complete signal is sent to circuit 32. Transmitter 34 then relays the information to receiver 42 for data collection. Other materials/devices may be used to detect relative position of the plunger 25.

With reference to the upper right portion of FIG. 6A, information source 24 can be an RFID tag with an antenna that can be connected or disconnected by a switch. With this arrangement, a switchable RFID tag information source 24 can be provided with the antenna disconnected. When medication container 20 is connected to medication port 13 the antenna becomes connected (switched ON) and the information source 24 can be read by an RFID reader identification sensor 18 within housing 4.

FIG. 6B is a magnified view showing a fully engaged information source 24 in close proximity to emitter (E) and detector (D) elements of identification sensor 18 and Hall Effect sensor 33 all contained within the housing 4.

Figure 7A:
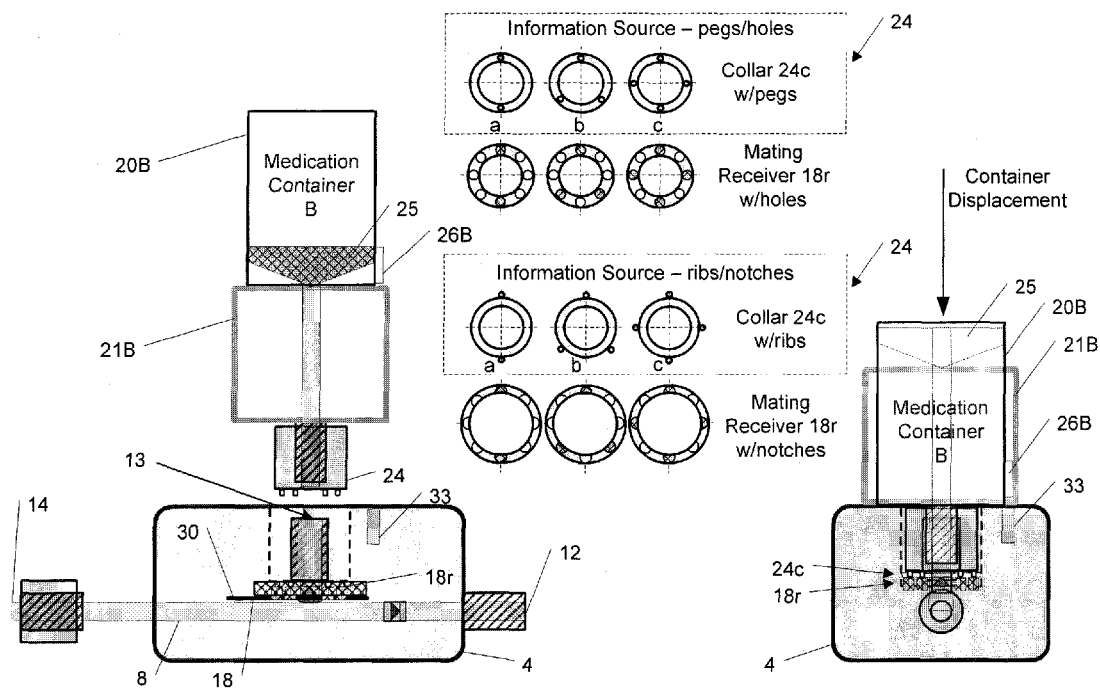
FIG. 7A is a diagram illustrating a medication container containing an information source that has mechanical features.
Figure 7B:
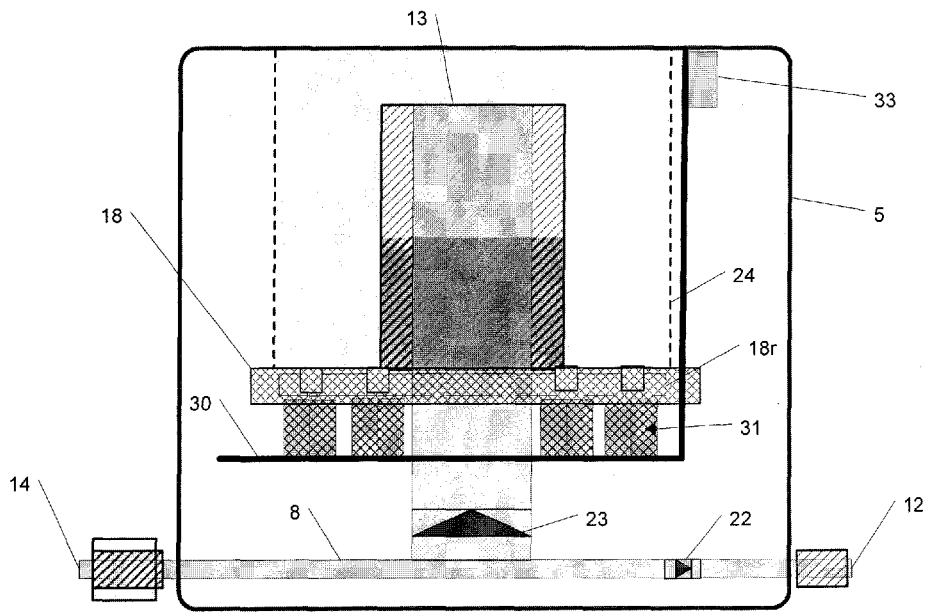
FIG. 7B is a diagram illustrating a magnified view of elements shown in FIG. 7A.

FIGS. 7A and 7B illustrate medication container 20B and injector housing 21B being a reverse syringe design wherein plunger 25 remains fixed relative to the motion of medication container 20B during medication administration. FIG. 7A on the left shows the medication container 20B with medication information source 24 affixed on the luer fitting tip before connection to medication port 13. Similar to medication container 20A, there can be a number of mechanical embodiments (a, b, c) for information source 24 on medication container 20B. Additionally, medication container 20B can contain an indicator 26B that can be ferric material that can be detected by magnetic sensor 33. The ferric material 26B can be a magnet or other type iron material matched with ferric material type sensor 33. Other types of indicators such as optical, capacitive, mechanical, etc. which are not ferric based can be used to indicate the completion of medication administration. When the medication delivery is completed as shown to the right medication container 20B with ferric material 26B comes into close proximity for detection by sensor 33 and a medication administration complete signal (or other data) can be sent to circuit 32. Transmitter 34 then relays the information to receiver 42 for data collection.

Indicator 26B can, in some implementations, be a switchable RFID tag with an antenna that can be connected or disconnected (see FIG. 6A). In this variation, an RFID tag indicator 26B can be provided with the antenna disconnected. When medication container 20B is fully displaced the antenna can become connected (switched ON) and the medication delivered indicator 26B can be read by an RFID reader within sensor circuit 30.

FIGS. 7A and 7B illustrate a variation in which information source 24 comprises a collar 24c with mechanical indicator pegs. FIG. 7A illustrates top and front view of housing 4. As shown to the left, medication container 20B is about to be coupled to medication port 13. A side view is depicted in the lower right such that medication container 20B is fully engaged with medication port 13. Collar 24c can have one or more indicator pegs arranged such as to indicate the type of medication contained in medication container 20B. Any number of pegs and/or peg patterns (a, b, c) can be used as an indication of the type of medication contained. Housing 4 can include a receiver identification sensor 18r that has opening holes to receive the pegs on collar 24c. Any number of opening patterns (a, b, c) can be used as an indication of the type of medication contained, the volume of medication, and/or expiration data. When properly engaged, pegs on collar 24c mate with receiver identification sensor 18r openings and form the medication information transfer. The pattern indicated is detected by identification sensor 18 and a signal can be sent to circuit 32. Transmitter 34 can then relay the information to receiver 42 for data collection.

Information source 24c can alternatively have external indicator ribs (or similar type of protrusions). Information source 24c can have one or more indicator ribs arranged such as to indicate the type of medication contained in medication container 20B or other relevant information. Any number of ribs and/or rib patterns (a, b, c) can be used as an indication of the type of medication contained. Housing 4 can include a receiver identification sensor 18r that has opening notches to receive the ribs on information source 24c. Any number of opening patterns (a, b, c) can be used as an indication of the type of medication contained. When properly engaged, ribs on information source 24c can mate with receiver identification sensor 18r notches or other features. The pattern indicated by receiver information source 18r can be detected by identification sensor 18 so that a signal containing data characterizing the medication container 20 is sent to circuit 32. Transmitter 34 then relays the information to receiver 42 for data collection.

FIG. 7B is diagram illustrating a magnified view showing a fully engaged information source 24 in close proximity to emitter (E) and detector (D) elements 31 of sensor circuit 30 and sensor 33 all contained within the housing 4. Information source 24c can have protrusions (in this case four pegs) protruding from the collar 24c. Receiver identification sensor 24r can mate with pegs on information source 24c facilitating detection of the medication information by emitter (E) and detector (D) sensors mounted on sensor circuit 30. Additionally, sensor 33 is shown located on the uppermost part of housing 4 for the detection of ferric material 26B.

FIGS. 8A, 8B and 8C depict a variation of information source 24. FIG. 8A depicts information source 24 formed as a flat disk mounted to the fluid outlet 17 of medication container 20. Information sensor 18 can be oriented vertically and detect information when medication container 20 is rotated about the fluid outlet axis. Information can be encoded using optical or magnetic methods. In one implementation, the information source 24 can carry a radial barcode pattern 29. Emitter/detector pairs 31 can detect information and signals can be provided to sensor circuit 30 that characterize the medication container 20.

FIG. 8B depicts information source 24 as a cylindrical/circumferential band having an outer surface that is mounted to the fluid outlet 17 of medication container 20. Information sensor 18 can be oriented horizontally and detect information when medication container 20 is rotated about a fluid outlet axis. Information can be encoded using optical or, magnetic methods. The band can have a barcode pattern that extends along the cylindrical surface at a constant radius. Emitter/detector pairs 31 can detect information and signals characterizing the medication container 20 can be provided to sensor circuit 30.

FIG. 8C depicts a magnified view of elements shown in FIG. 8A. An attachment material 37 can be interposed between medication container 20. The attachment material 37 can configured to be releasable from a first medication container and re-attached to a second medication container. This feature can be used when an original medication container (medication vial) is provided without a fluid outlet and a second medication container (syringe) is used to withdraw medication from the first medication container (vial) for use with medication injection site 3. The information source 24 originally provided with the first medication container (vial) can be removed and then attached to the second medication container (syringe) during the medication transfer process. The contents of the second medication container 20 can be injected into the medication port 13 and information can be detected by information sensor 18.

Figures 9A, 9B, 9C:
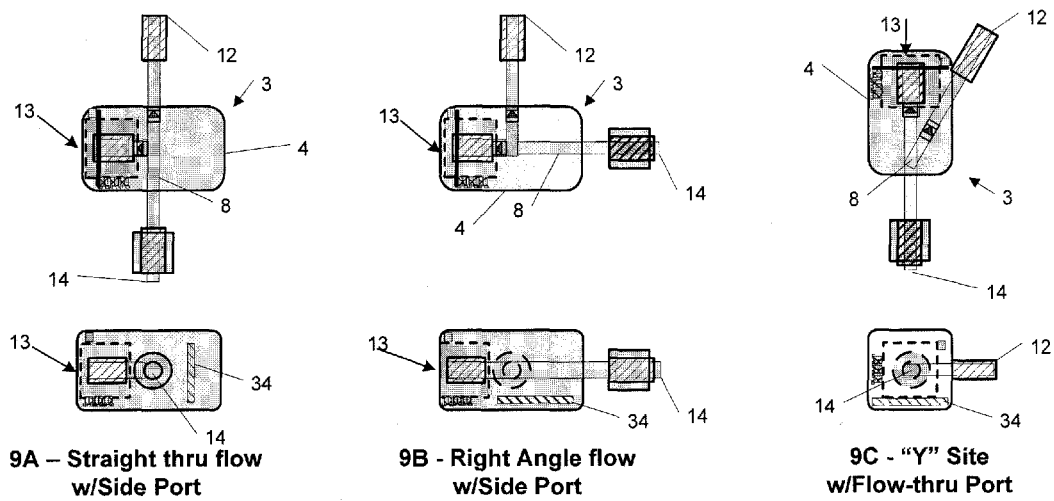
FIG. 9A is a diagram illustrating a medication injection site with a linear first fluid channel intersected by a second fluid channel at right angle.
FIG. 9B is a diagram illustrating a medication injection site with a first fluid channel intersected by a second fluid channel at right angle and a medication port coupled to the intersection of the first fluid channel and the second fluid channel.
FIG. 9C is a diagram illustrating a medication injection site with a first fluid channel intersected by a second fluid channel at an acute angle.

FIGS. 9A, 9B and 9C depict top and front views of alternate construction embodiments of the fluid junction elements and housing 4. FIG. 9A shows housing 4 with a straight through first fluid channel 8 with a side access for medication port 13. FIG. 9B shows housing 4 with a right angled first fluid channel 8 with a side access for medication port 13. FIG. 9C shows housing 4 with a "Y" first fluid channel 8 and a straight through medication port 13. Various other configurations can be constructed with different positioning of inlet 12, outlet 14 and medication port 13 to facilitate any requirements of the clinical set-up, orientation of hospital equipment, and/or medical practitioner preference. FIG. 9A depicts a configuration that is a typical extension set facilitating an in-line attachment from tubing set 11 to a patient's catheter. FIG. 9B depicts a configuration that facilitates connection to a manifold (outlet 14) and allows straight through injections into medication injection port 13. FIG. 9C depicts a configuration that is a typical "Y" site arrangement facilitating location of medication port 3 on tubing set 11.

Figure 10A:
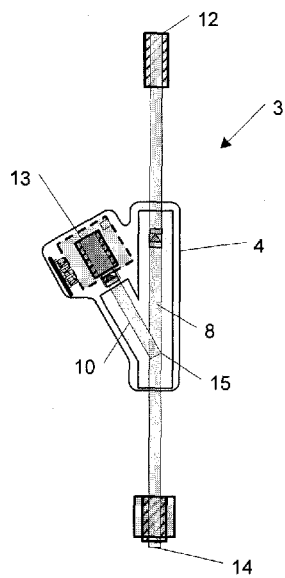
FIG. 10A is a diagram illustrating a fluid delivery tubing set.
Figure 10B:
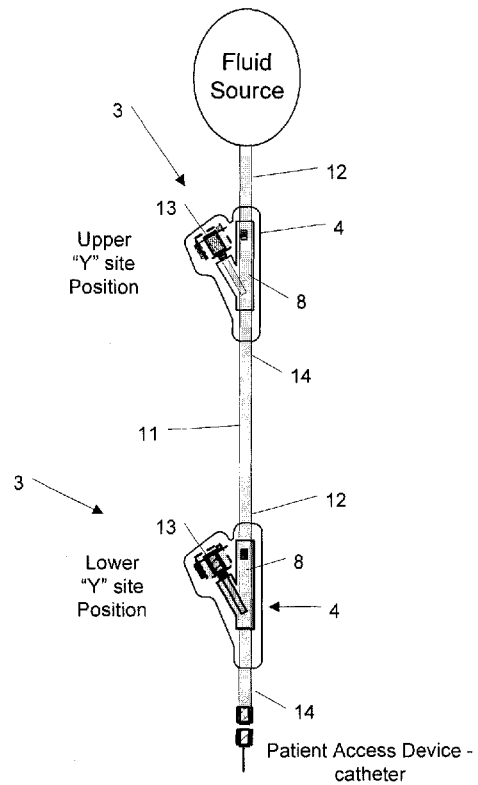
FIG. 10B is a diagram illustrating different locations for a fluid delivery tubing set as in FIG. 10A.

FIGS. 10A and 10B depict alternate variations for housing 4 as mounted on fluid delivery tubing sets. FIG. 10A depicts a "Y" site adapter configuration. Here inlet 12 and outlet 14 can be separated by an extended conduit 8 to form an extension set. FIG. 10B depicts a complete fluid delivery tubing set with inlet 12 being a fluid bag spike and outlet 14 a connector to a patient access device. The housing 4 can be located near the fluid source bag at an upper "Y" site or nearer the patient at a lower "Y" site location. Multiple configurations (e.g., two or more medication injection sites used for a single patient, etc.) allow for greater access for tubing set medication injection during medical procedures when several practitioners are simultaneously working on a patient (and access to on particular medication injection site may be impeded). Other configurations can be utilized as a function of the clinical setting physical space and access to the tubing set.

Figure 11A:
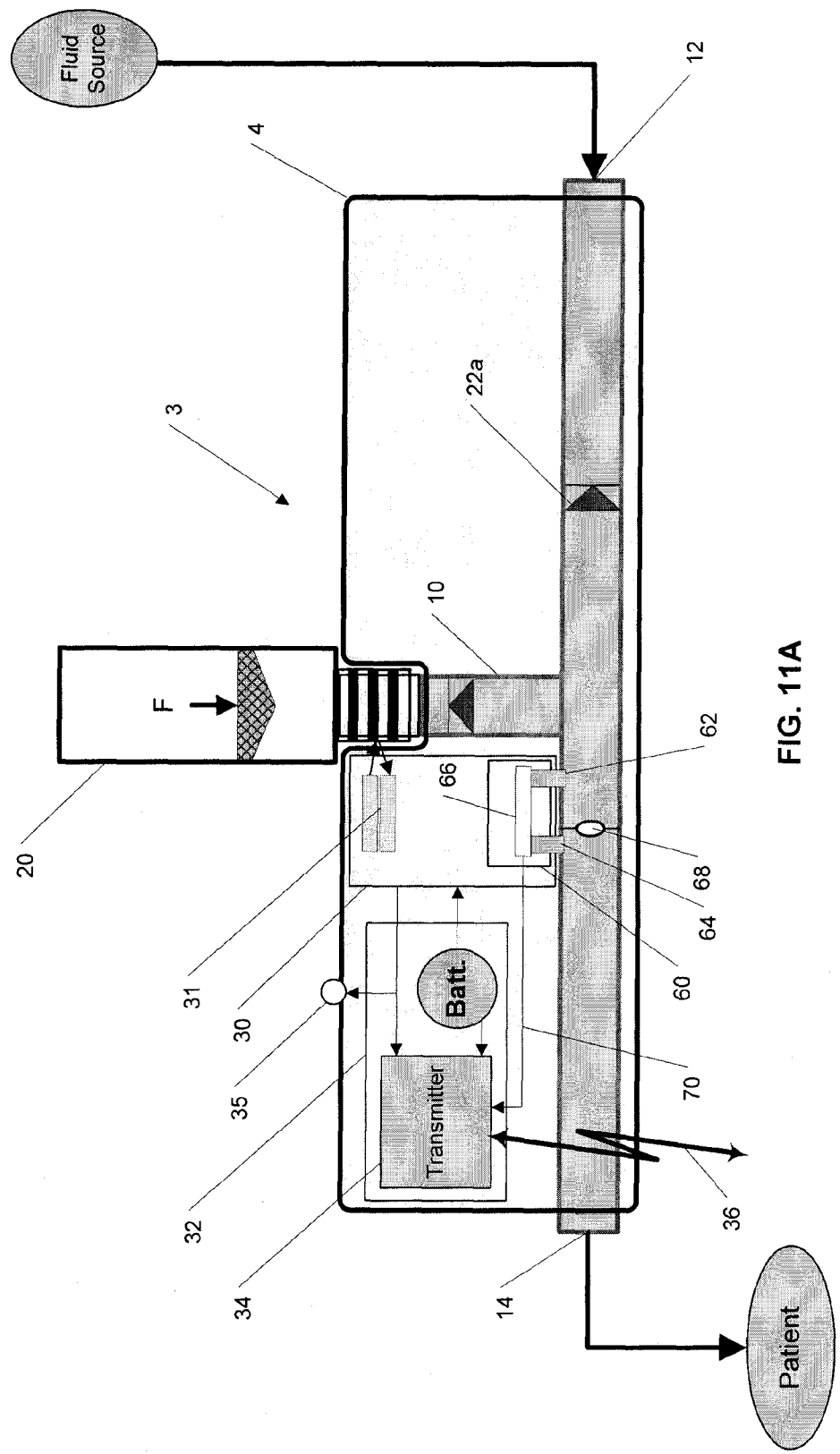
FIG. 11A is a diagram illustrating a medication injection site with a fluid flow measurement sensor on a first fluid channel.
Figure 11B:
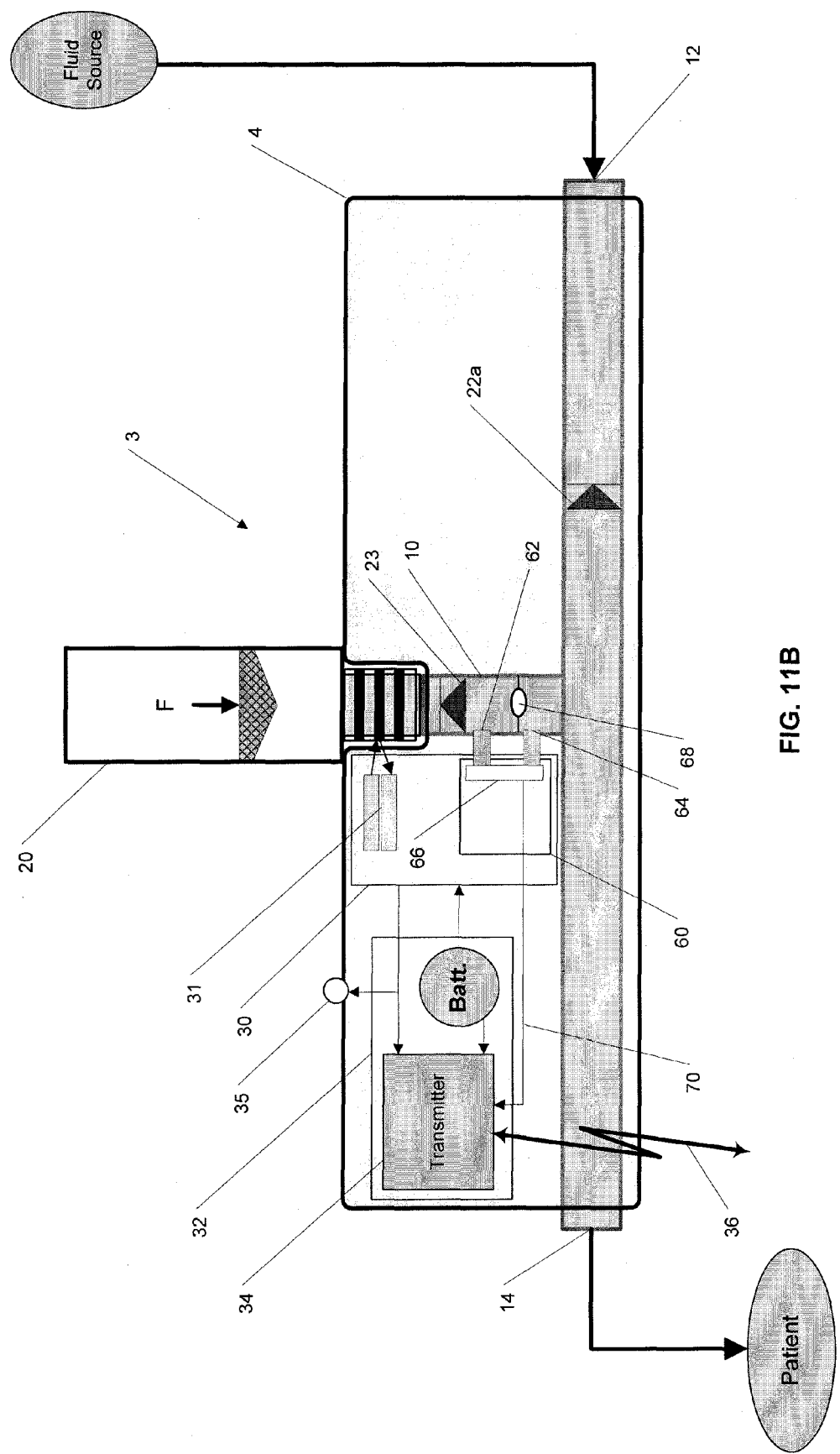
FIG. 11B is a diagram illustrating a medication injection site with a fluid flow measurement sensor on a second fluid channel.

FIGS. 11A and 11B depict a medication injection site 3 incorporating fluid flow sensor 60. The fluid flow sensor 60 can be a pressure measurement sensor with differential pressure inlets 62 and 64 that are fluidically connected to first fluid channel 8. Pressure transducer 66 can provide a differential pressure signal 70. When medication container 20 delivers fluid to the second fluid channel 10 there is a sudden increase in differential pressure signal 70 due to the fluid flow through orifice 68. This change in differential pressure indicates fluid delivery from medication port 13 is occurring. The value of differential pressure signal 70 can be provided to transmitter 34 and subsequently transmitted to receiver 42 as shown in FIG. 5. Pressure signal 70 can be sent to message decoder & display driver 46. Micro-computer 47 can contain algorithms to calculate fluid volume delivered based on the differential pressure. When the volume delivered equals the original volume in container 20 the end of medication delivery is logged. Knowing differential pressure, time, cross-sectional area of orifice 68 and cross-sectional area of first fluid channel 8 enables calculation of fluid volume delivered.

A variation of the medication injection site 3 system of FIG. 5 is shown in FIG. 11B and depicts a construction with the pressure transducer 66 positioned on second fluid channel 10 instead of on first fluid channel 8. Fluid inlets 62 and 64 can be located down stream or upstream of check valve 23. In this configuration, orifice 68 is located in second fluid channel 10 between inlets 62 and 64. Volume delivered is calculated in the same way as above using algorithms in micro-computer 47.

In other constructions, the fluid flow sensor 60 can include a single channel pressure transducer 66. In this variation, volume can be calculated as the integral of the pressure increase over time.

Figure 12:
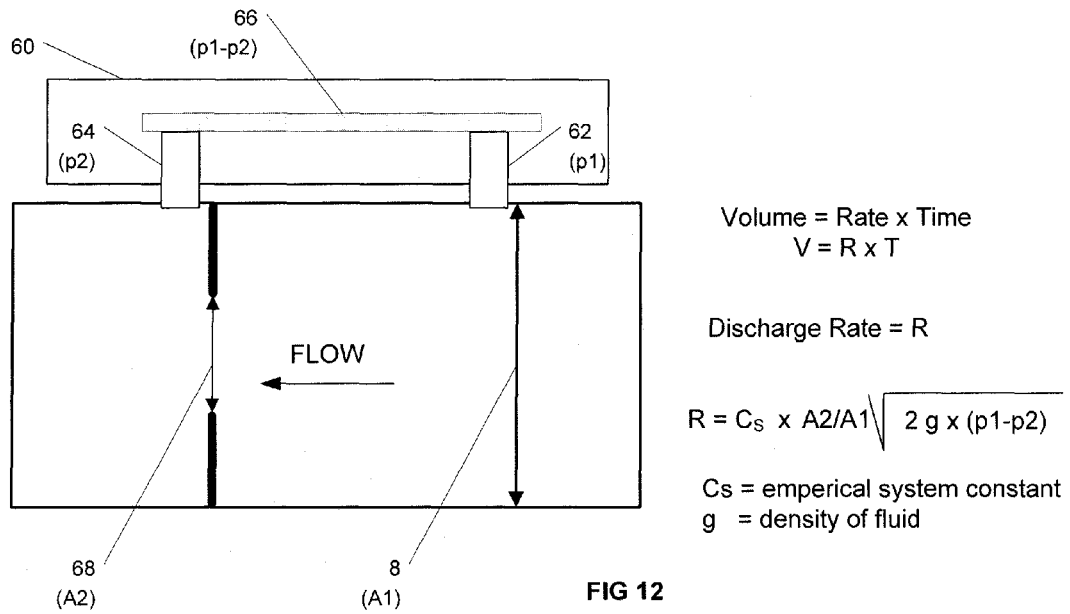
FIG. 12 is a diagram illustrating a flow measurement calculation method described for use with a medication injection site as in FIGS. 11A and 11B.

FIG. 12 depicts a detailed view of the pressure measurement components 62, 64 and 66 and orifice 68. Calculation of volume can be based upon the Bernoulli Equation and Volume=Rate×Time. The discharge rate R is calculated using the formula shown in FIG. 12 to the right where $C_s$ is an empirically derived constant for calibrating the system, A2/A1 is the ratio of the areas of orifice 68 (A2), first fluid channel 8 (A1) and "g" is the fluid density. The differential pressure 66 can be the pressure difference between inlet 62 (p1) and inlet 64 (p2). It can be assumed that density "g" of the fluid in medication container 20 is that of water. However, other fluids with other densities can be used and calculations adjusted accordingly. Volume calculation can be completed within circuit 60 before wireless transmission or circuit 44 (not shown) after wireless transmission.

In some variations, fluid delivery sensor 60 can be used to directly sense fluid flow. Such a fluid delivery sensor 60 can based upon one of a paddle wheel flow meter, a turbine flow meter, a thermal flow meter, an ultrasonic flow meter, etc.

Figure 13A:
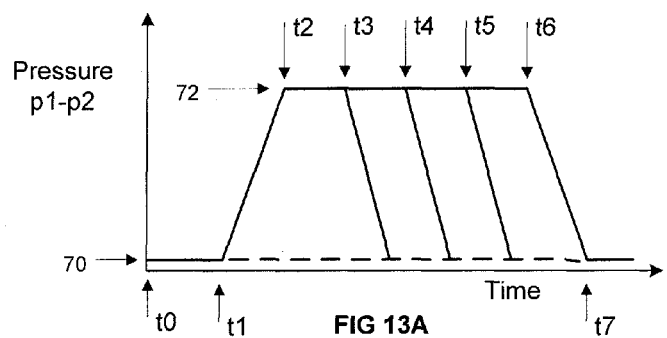
FIG. 13A is a diagram illustrating a first pressure-time graph for a flow measurement calculation method as in FIG. 12.
Figure 13B:
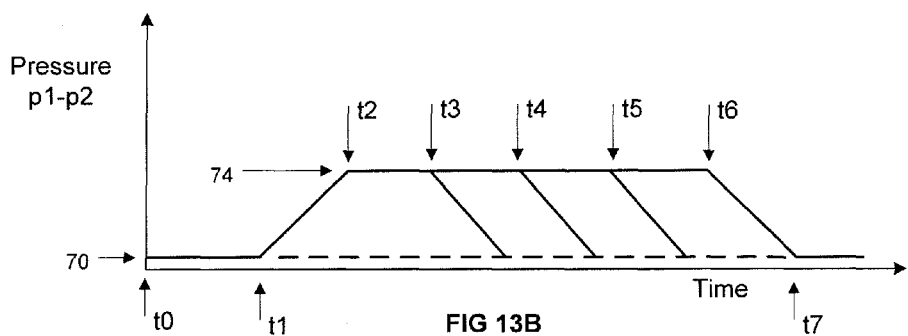
FIG. 13B is a diagram illustrating a second pressure-time graph for a flow measurement calculation method as in FIG. 12.

FIGS. 13A and 13B depict differential pressure-time graphs at various points in the operation of system shown in FIGS. 11A and 11B. FIG. 13A depicts a normal pressure time graph. Initially at time t0, pressure is at level 70 with no force applied to the medication container 20. At time t2 when the user increases force F by pressing on the plunger rod of a syringe or the medication container 20 of a reverse syringe, differential pressure increases from 70 to 72 at time t2 indicating user activity. This higher pressure 72 is sustained over time from t2 to t6 when the pressure returns to level 70 at time t7 when the medication administration is completed. The volume calculated confirms that the medication has been delivered. If the pressure is only maintained from t2 to t3 then an incomplete volume has been delivered. Various time points t3, t4, t5 and t6 are indicative of 25%, 50%, 75% or 100% volume delivered respectively. The volume calculation can be displayed to the user providing feedback on volume delivered and time stamp logged as a partial dose of medication.

FIG. 13B depicts a different pressure-time graph where the pressure is lower, indicative of slower delivery of medication. At time t1 the initial pressure 70 increases to level 74 which is less than pressure level 72 in FIG. 13A. The pressure is maintained for a longer period of time thru t3, t4, t5, and t6 where the pressure then decreases back to level 70 at time t7. Similarly as shown in FIG. 13A, if pressure is not sustained but instead drops down prematurely at t3, t4 or t5 an incomplete volume is calculated. There can be a number of other combinations of times and differential pressures used in calculating volume.

Figure 14A:
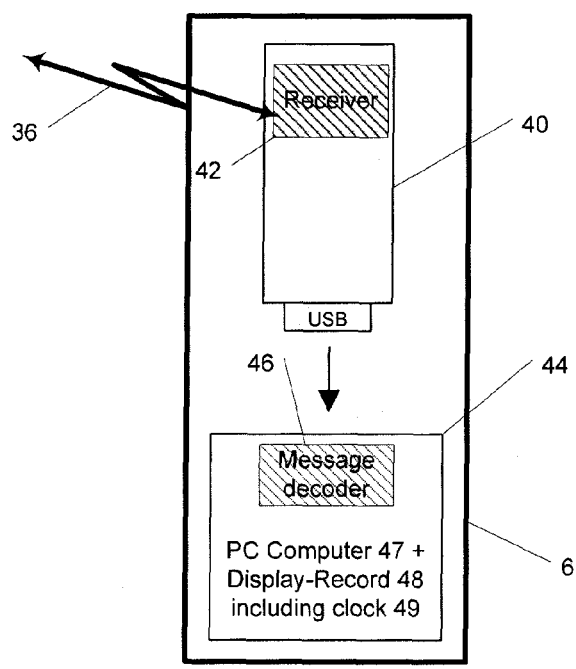
FIG. 14A is a diagram illustrating a data collection system with a wireless data receiver and removable memory.
Figure 14B:
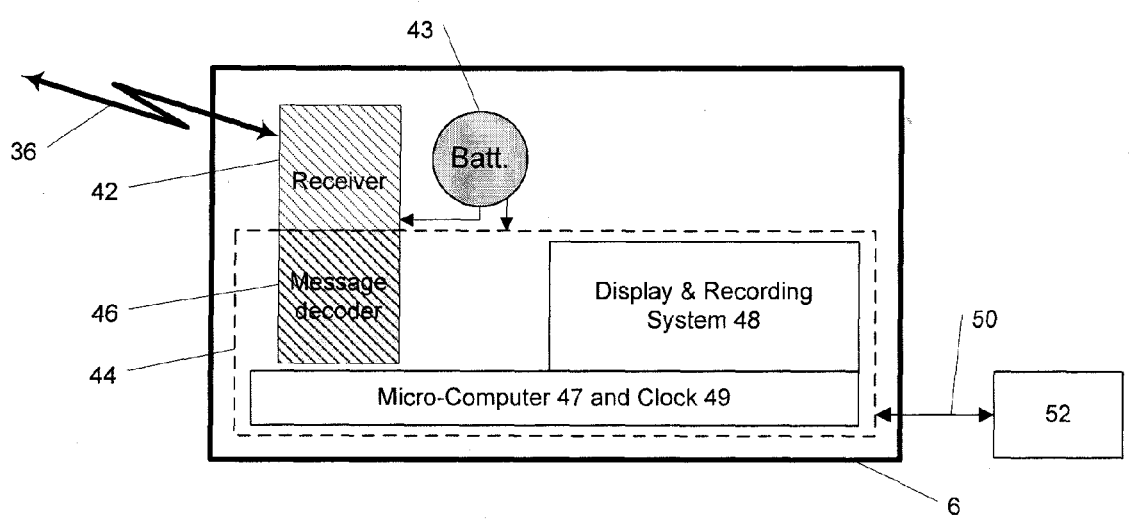
FIG. 14B is a diagram illustrating a data collection system with a wireless data receiver, a display, and a recording system.

FIGS. 14A and 14B depict two variations of data collection system 6. Display and recording system 48 can include any combination of hardware and software to receive signals from transmitter 34 and records the sequence of medication administrations. Receiver 42 can be a receiver only or a transceiver (i.e., a combined transmitter-receiver, etc.).

With reference to FIG. 14A, data collection system 6 can include a general purpose personal micro-computer 47 with a USB connection to receiver 42. In another embodiment shown in FIG. 14B, data collection system 6 can be stand alone and powered by a self-contained power source 43. FIG. 14A depicts a general purpose USB device with receiver 42 mounted in a USB housing with USB connection to a standard micro-computer 47 and message decoder 46. Information 36 received by receiver 42 is USB transferred to an external micro-computer 47. Software in message decoder 46 and micro-computer 47 can process information 36, add a time stamp from clock 49 and displays and logs the information via information display and recording system 48. Display, recording and logging function software is located in micro-computer 47. Micro-computer 47 can provide information 50 to a medical information system 52 as shown in FIG. 5.

FIG. 14B depicts a more integrated, self-contained and dedicated data collection system 6. Receiver 42, message decoder 46, micro-computer 47, display and recording system 48, clock 49 and micro-computer 47 are combined into one module. Receiver circuit 42, message decoder 46 and display and recording system 48 can be operated by micro-computer 47. A self-contained power source 43 provides energy for mobile operation.

Information circuit 44 can include or otherwise use software to provide the data collection system functions. When data collection system 6 is not functional or energized or when a patient is transferred from one data collection system 6 to a second data collection 6 memory 38 provides a history of medication administration data as discussed above. In this case second data collection system 6 can receive a medication administration data history and timer counts between subsequent medication administrations. The software automatically associates the medication administrations with real time from clock 49. Display recording system 48 is configured to process the previously recorded data, time stamp, log and display the information for the user.

Additionally, the software within data collection system 6 can include stored information in support of a series of medication administrations based upon an acute care protocol. Thus, the software can display stored messages based upon medication injections in support of acute care protocol providing health care providers guidance in the conduct of the protocol.

Care protocols, such as acute care protocols, can be updated periodically, annually, or when studies indicate a need for updating. Information circuit 44 can be configured to receive updated information 50 from a medical information system 52 that is indicative of the most recent acute care protocols or protocol updates. Information circuit 44 software is in turn configured to update itself pursuant to the update information. The updated information can improve any operational aspect of the software.

While the discussion above describes an arrangement in which "raw" data is transmitted from the medication injection site 3 to the data collection system 6 so that micro-computer 47 can process such raw data to identify traits such as patient identification (e.g., serial number or other unique identifier of medication injection site 3), medication container contents, volume, expiration date, and/or pressure or volume information, it will be appreciated that one or more of such traits can be determined by the medication injection site 3. For example, memory 38 may contain mapping data which associates raw data generated by identification sensor 18 into one or more of: an identification of the patient or the medication injection site 3 (e.g., serial number, etc.), contents of medication container 20, volume of medication container 20, or expiration date of the contents of medication container 20. This information can then be transmitted by transmitter 34 to data collection system 6.

Figure 15:
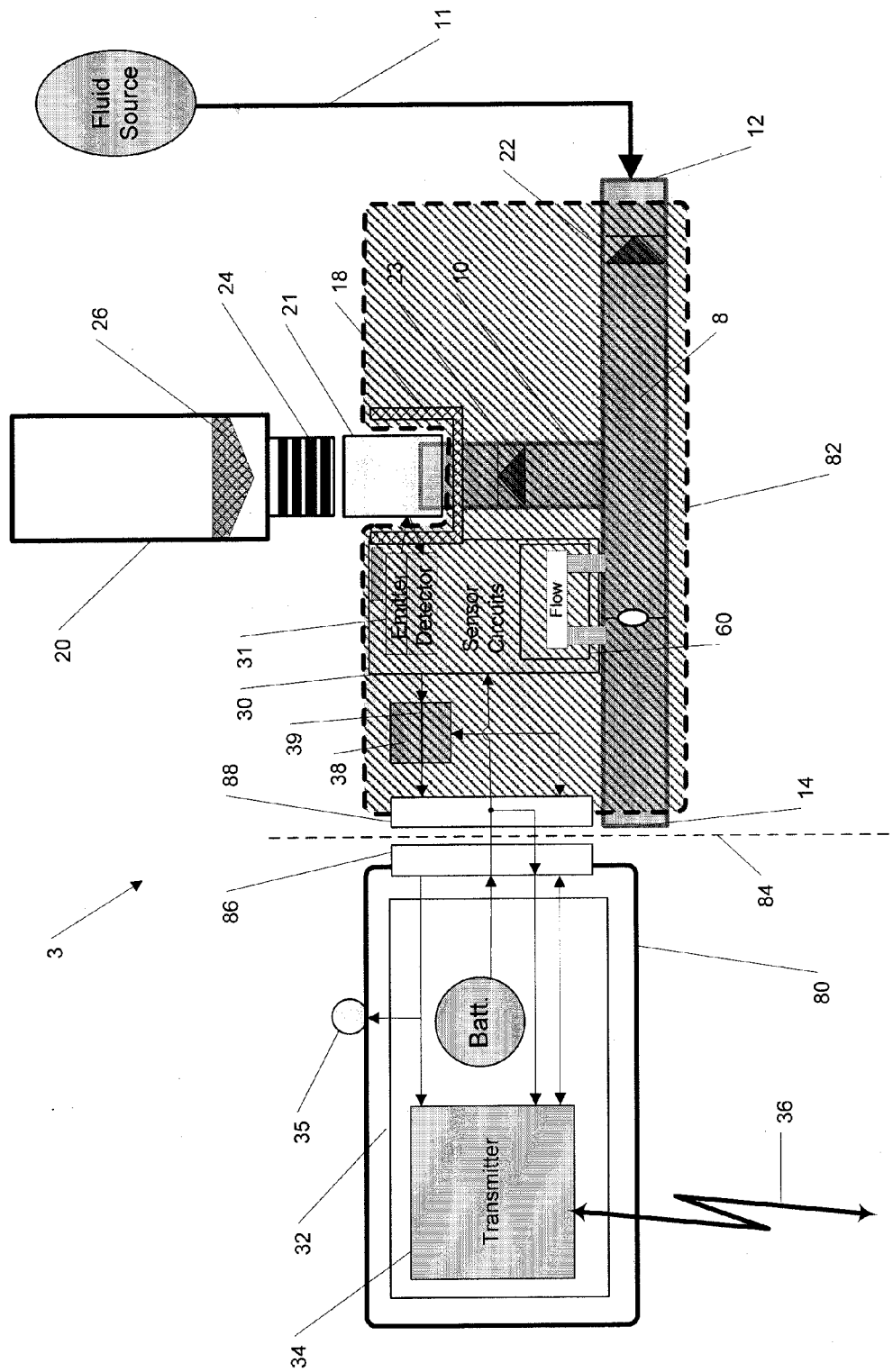
FIG. 15A is a diagram illustrating a first variation of medication injection site that includes a disposable sub-housing and a reusable sub-housing.
FIG. 15B is a diagram illustrating a second medication injection site that includes a disposable sub-housing and a reusable sub-housing.
FIG. 15C is a diagram illustrating a third medication injection site that includes a disposable sub-housing and a reusable sub-housing.
Figure 15:
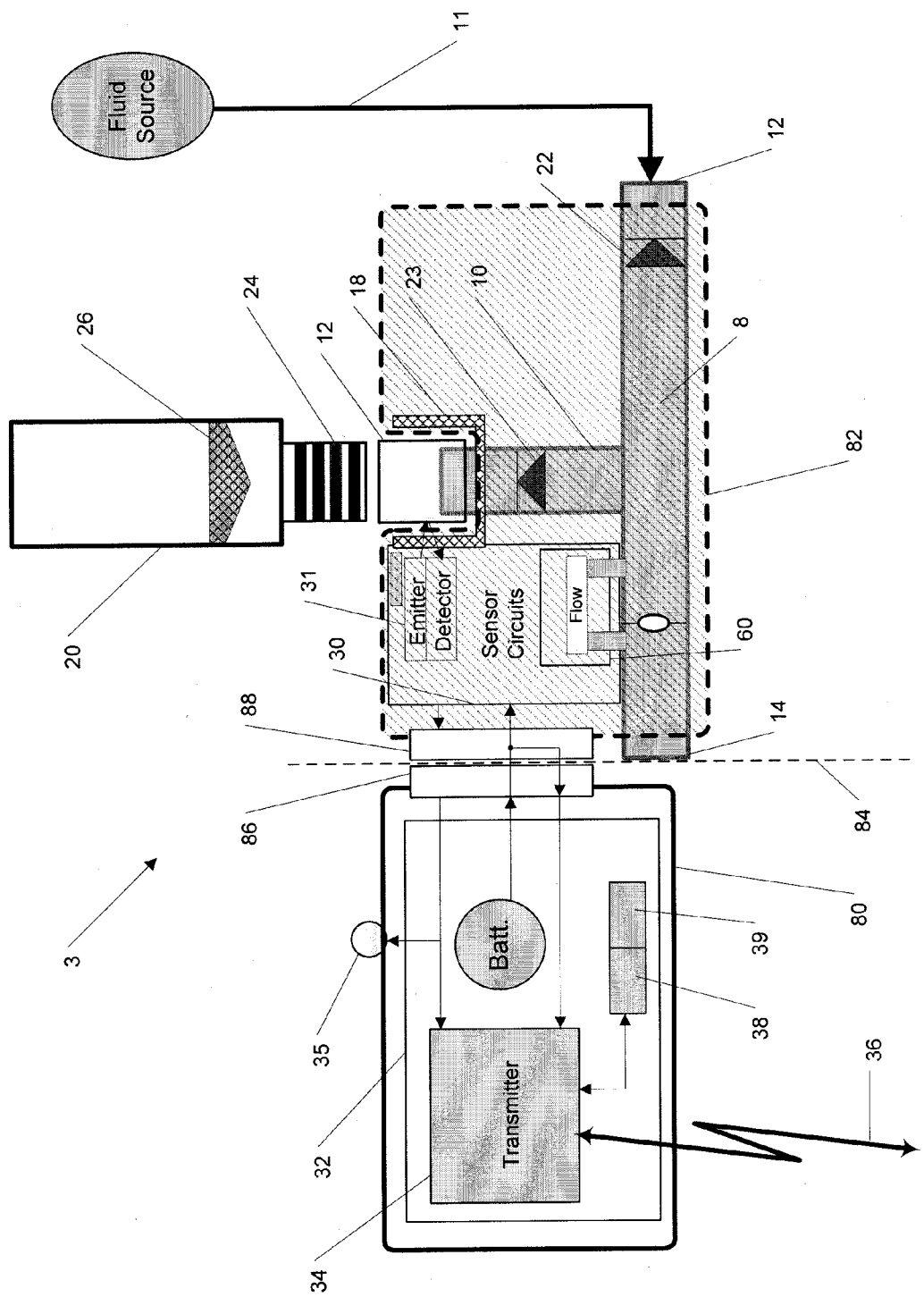
Figure 15:
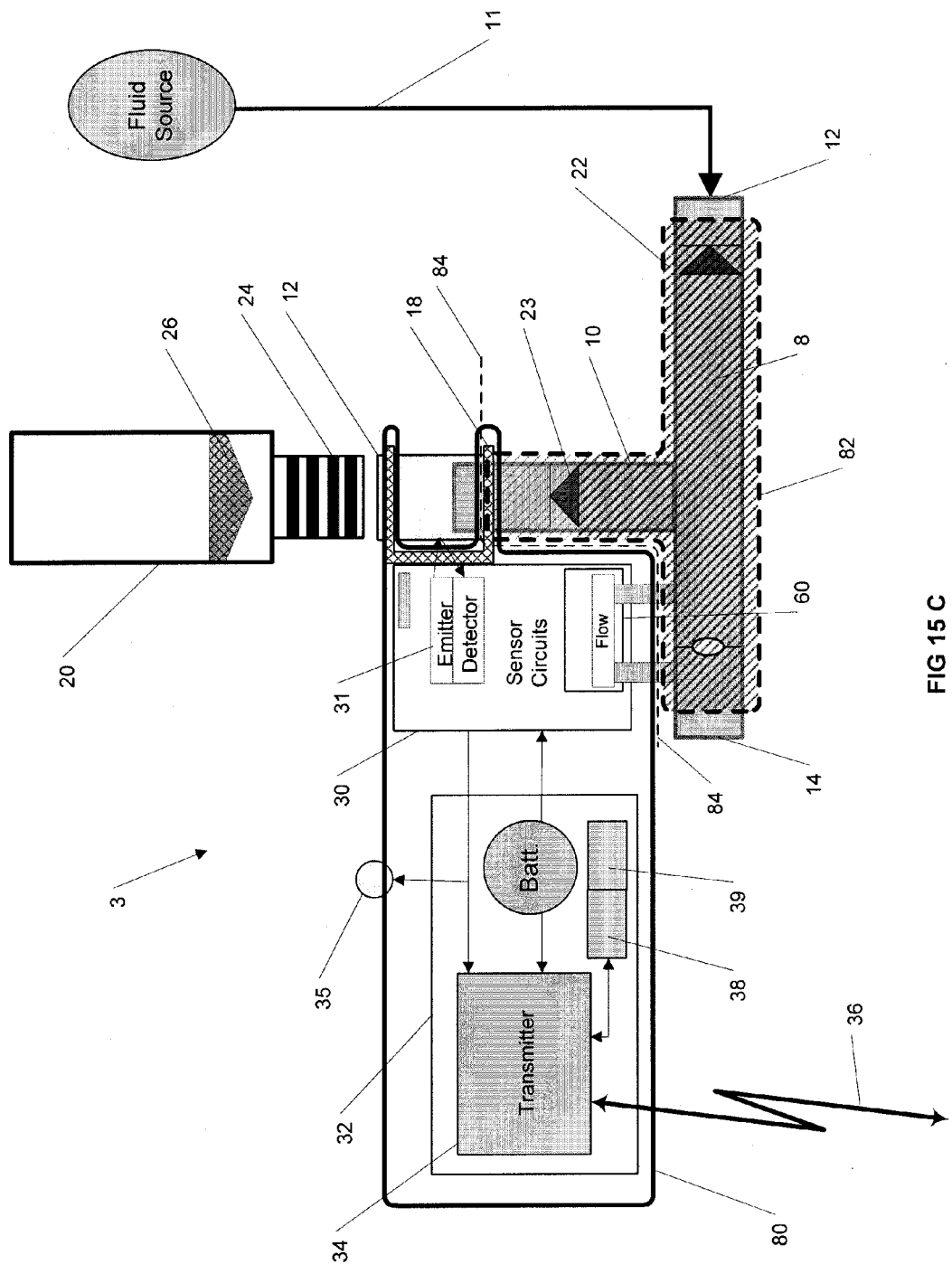

FIGS. 15A, 15 B and 15C depict housing 4 as shown in FIG. 3A separated into reusable sub-housing 80 and disposable sub-housing 82. Various constructions can be utilized that distribute elements of medication injection port 3 either to reusable sub-housing 80 or to disposable sub-housing 82. Three variations are described below, however, other implementations can be adopted based on considerations such as overall size, weight, per-patient costs, etc. When used, reusable sub-housing 80 is connected to disposable sub-housing 82 through interface 84. When connected, medication injection site 3 becomes functional by providing power from power source "Batt". When the power source is contained in reusable sub-housing 80 a charging element (not shown) can be configured to recharge the power source between uses. When the power source is self-contained within disposable housing 4 no recharging is needed (see FIGS. 3A, 4A and 5).

FIG. 15A depicts a first sub-housing implementation in which reusable sub-housing 80 can include one or more of: transmitter 34, battery, indicator 35 and connector 86. In this variation, disposable sub-housing 82 can include one or more of: memory 38, timer 39, sensor circuit 30, emitter/detector 31, flow sensor 60, identification sensor 18, first fluid channel 8, second fluid channel 10, check valve 22, check valve 23 and connector 88. Interface 84 can be formed by mating connector 86 with connector 88 and can be one or more of an electrical contact, a mechanical contact, an optical coupling or a magnetic coupling.

FIG. 15B depicts a second sub-housing implementation in which reusable sub-housing 80 can include one or more of: transmitter 34, battery, indicator 35, memory 38, timer 39 and connector 86. Disposable sub-housing 82 can include one or more of: sensor circuit 30, emitter/detector 31, flow sensor 60, identification sensor 18, first fluid channel 8, second fluid channel 10, check valve 22, check valve 23 and connector 88. Interface 84 can be formed by mating connector 86 with connector 88 and can be one or more of an electrical contact, a mechanical contact, an optical coupling or a magnetic coupling.

FIG. 15C depicts a third sub-housing implementation in which reusable sub-housing 80 can include one or more of: transmitter 34, battery, indicator 35, memory 38, timer 39, sensor circuit 30, emitter/detector 31, flow sensor 60 and identification sensor 18. Disposable sub-housing 82 can include one or more of: first fluid channel 8, second fluid channel 10, check valve 22, and check valve 23. Interface 84 can be formed by one or more of a hydraulic coupling, a mechanical coupling, an optical coupling or a magnetic coupling.

Figure 16A:
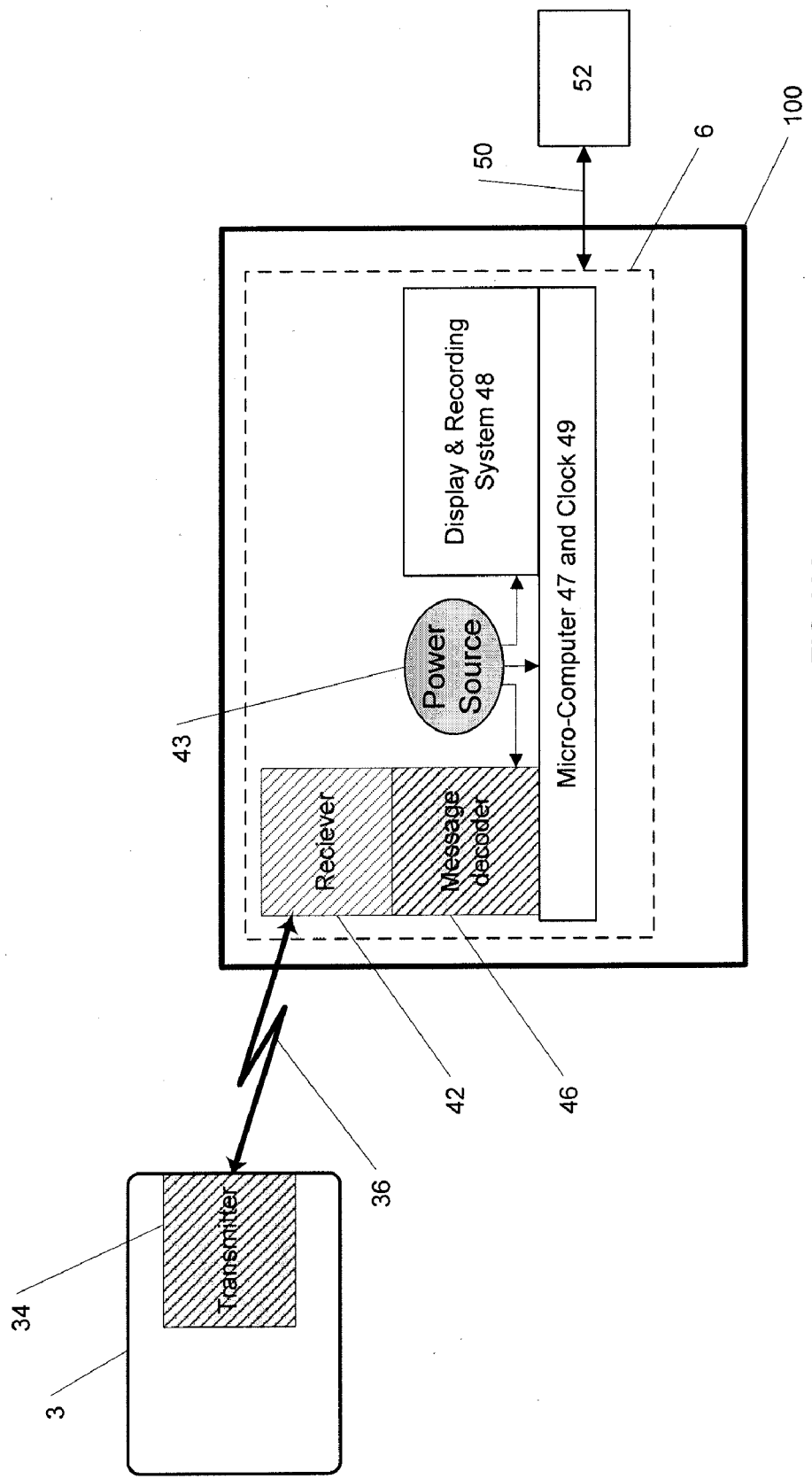
FIG. 16A is a diagram illustrating a secondary medical device configured to receive wireless information from a medication injection site.
Figure 16B:
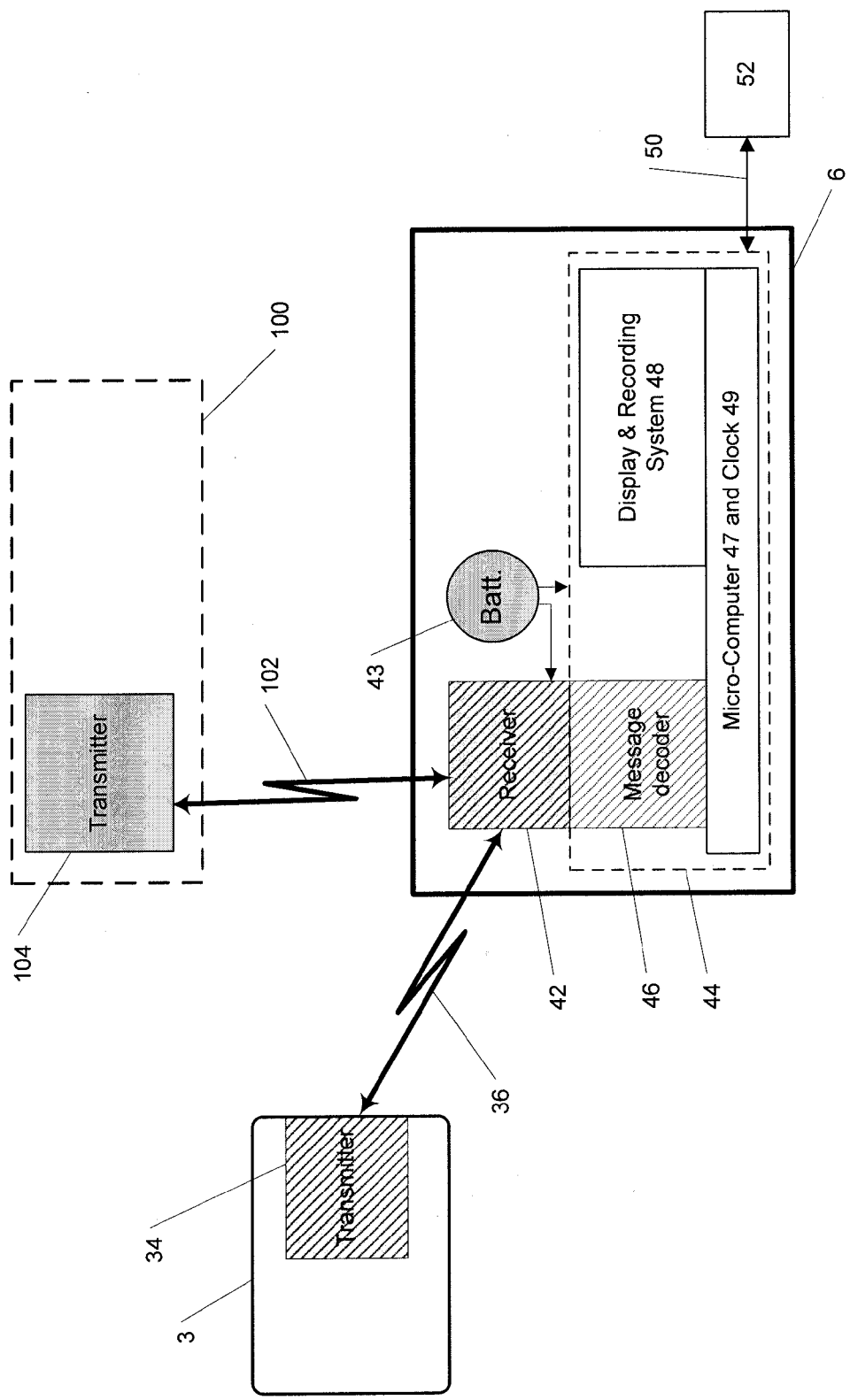
FIG. 16B is a diagram illustrating a data collection system to receive wireless information from a medication site and from a secondary medical device.
Figure 16C:
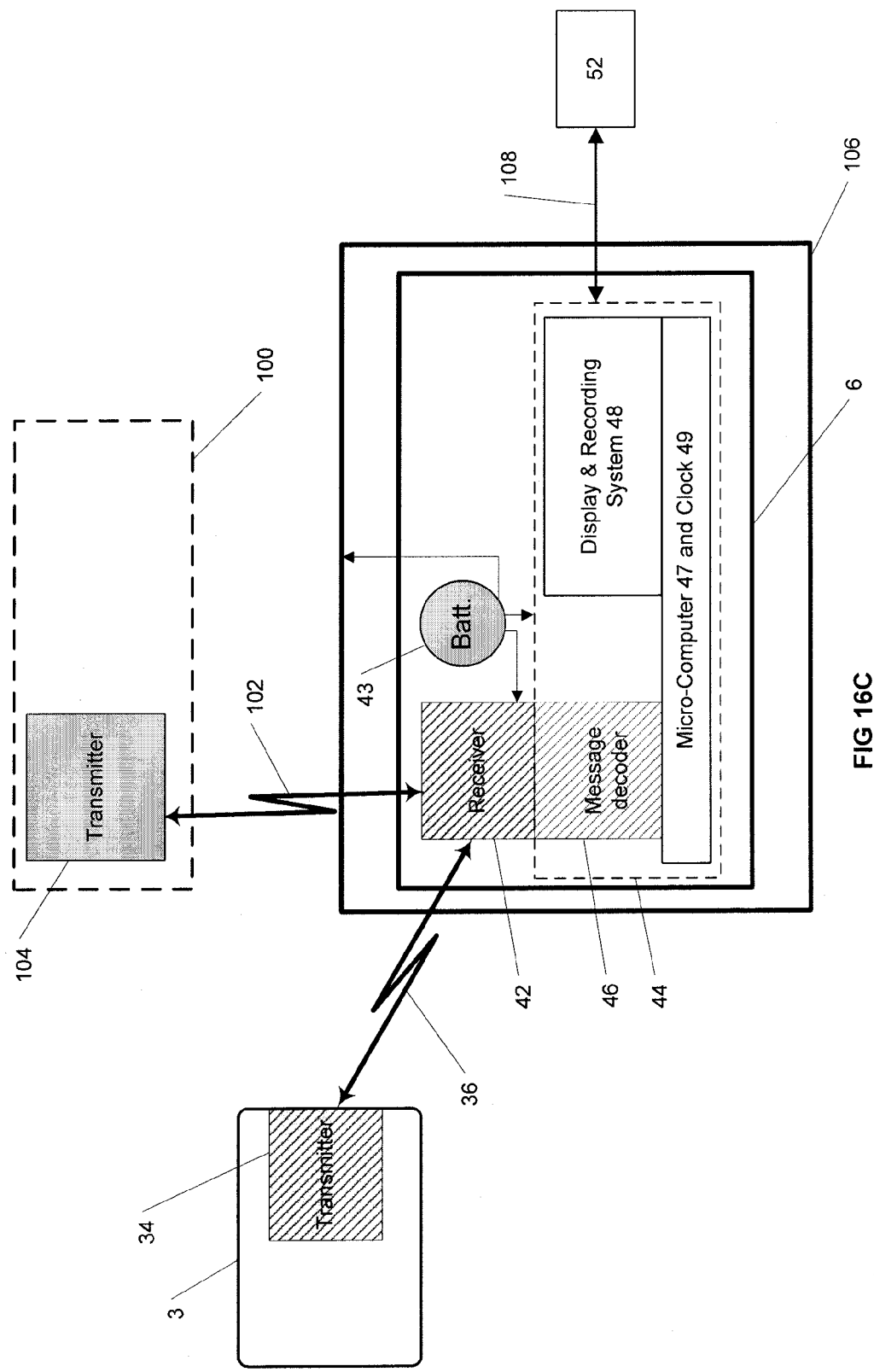
FIG. 16C is a diagram illustrating a data collection system configured as a cellular phone to receive wireless information from a medication injection site and/or a secondary medical device.

FIGS. 16A, 16B and 16C depict three additional variations of data collection system 6. FIG. 16A depicts a variation of a data collection system in which data collection 6 is coupled to or forms part of a secondary medical device 100 such as an EKG monitor, a defibrillator, a pulse oximeter, an $ETCO_2$ monitor or an IV pump. Data collection system 6 can receive medication administration data information 36 by receiver 42. Information 36 is processed through message decoder 46 to micro-computer 47. The software automatically associates the medication administrations with real time using clock 49. Display recording system 48 can process the previously recorded data, time stamp, log and display the information for the user. The secondary medical device 100 can provide information 50 such that it transfers medication administration information 36 from recording system 48 to medical information system 52.

FIG. 16B depicts another variation of a data collection system 6 that can wirelessly receive information 102 from a secondary medical device 100 such as an EKG monitor, a defibrillator, a pulse oximeter, an $ETCO_2$ monitor or an IV pump. In this configuration, transmitter 104 within medical device 100 transmits information 102 to receiver 42 within data collection system 6. Information 102 is processed through message decoder 46 to micro-computer 47 and is time stamped by clock 49. This information is integrated in time with medication administration information 36 and is displayed and logged by recording system 48. The user can be provided with integrated data from medication injection site 3 and medical device 100.

FIG. 16C depicts another variation of a data collection system 6 that can wirelessly receive information 36 from medication site 3 and a secondary medical device 100 such as an EKG monitor, a defibrillator, a pulse oximeter, an $ETCO_2$ monitor or an IV pump. In this configuration, transmitter 34 within medication site 3 transmits medication administration information 36 to receiver 42 within data collection system 6. Data collection system 6 can be coupled to or form part of a cellular phone 106. Additionally, data collection system 6 within cellular phone 106 can wirelessly receive information 102 from a secondary medical device 100 such as an EKG monitor, a defibrillator, a pulse oximeter, an $ETCO_2$ monitor or an IV pump. Information 102 is processed through message decoder 46 to micro-computer 47 and is time stamped by clock 49. This information 102 is integrated in time with medication administration information 36 and is displayed and logged by recording system 48. The user can be provided with integrated data from medication injection site 3 and medical device 100. The cellular phone 106 can provide information 108 such that it transfers medication administration information 36 and medical device information 102 from recording system 48 to medical information system 52.

The subject matter described herein can be embodied in systems, apparatus, methods, and/or articles depending on the desired configuration. In particular, aspects of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows described herein do not require the particular order shown, or sequential order, to achieve desirable results. Other embodiments can be within the scope of the following claims.

What is claimed is:

1. A system comprising:
a housing comprising a reusable sub-housing and a disposable sub-housing, the reusable sub-housing being operatively coupled to the disposable sub-housing, wherein the reusable sub-housing is intended for use by a plurality of patients and the disposable sub-housing is intended for use by a single patient;
a medication port extending from an external face of the housing and configured to be fluidically and directly coupled to a fluid outlet of a manually injectable medication container;
an identification sensor disposed within the housing to generate identification information indicative of contents of the medication container when the fluid outlet of the medication container is being fluidically coupled to the medication port;
a transmitter disposed within the housing and in communication with the identification sensor to wirelessly transmit the information generated by the identification sensor to a remote data collection system; and
a power source disposed within the housing powering the identification sensor and the transmitter.

2. A system as in claim 1, further comprising a junction element at least partially extending within the housing forming a first fluid channel and a second fluid channel, the first fluid channel extending from a first end to a second end, the second fluid channel extending from a distal end and terminating at the first fluid channel at an intersection intermediate the first end and the second end.

3. A system as in claim 1, wherein the power source is disposed within the reusable sub-housing.

4. A system as in claim 3, wherein the identification sensor is disposed within the reusable sub-housing.

5. A system as in claim 4, wherein the transmitter is disposed within the reusable sub-housing.

6. A system as in claim 1 wherein the transmitter is a transceiver.

7. A system as in claim 1, wherein the disposable sub-housing is part of a kit including a sterile pouch enveloping the disposable sub-housing.

8. A system as in claim 2, wherein the first fluid channel and the second fluid channel are disposed within the disposable sub-housing.

9. A system as in claim 2, further comprising: a self-contained fluid delivery sensor disposed within the reusable sub-housing and in communication with the transmitter to characterize fluid flow through one or more of the first fluid channel and the second fluid channel, wherein the transmitter further wirelessly transmits data characterizing fluid delivery to the remote data collection system.

10. A system as in claim 1, further comprising: a processor disposed within the reusable sub-housing that is coupled to one or more of the identification sensor, the transmitter, and the power source.

11. A system as in claim 1, wherein the power source is self-contained, coupled to a remote power source, or is a rechargeable battery that can be detachably coupled to a remote charging source.

12. A system as in claim 1, wherein the housing has a shape and size enabling it to be held by a first hand of a user while the user administers medication from the medication container via the medication port using his or her second hand.

13. A system as in claim 1, wherein the reusable sub-housing is operatively coupled to the disposable sub-housing by a connection interface.

14. A system as in claim 13, wherein the connection interface includes one or more of an electrical contact, an optical coupling, a mechanical coupling, and a magnetic coupling.

15. A system comprising:
a housing;

a medication port extending from an external face of the housing configured to be fluidically and directly coupled to a fluid outlet of a manually injectable medication container;

an identification sensor disposed within the housing to generate identification information indicative of contents of the medication container when the fluid outlet of the medication container is being fluidically coupled to the medication port;

a transmitter disposed within the housing and in communication with the identification sensor to wirelessly transmit the information generated by the identification sensor to a remote data collection system, wherein the remote data collection system is coupled to or integral with a secondary medical device; and a power source disposed within the housing powering the identification sensor and the transmitter.

16. A system as in claim 15, wherein the secondary medical device is selected from a group comprising: a physiological sensor, a defibrillator, an infusion pump, a ventilator, an anesthesia machine.

17. A system as in claim 16, wherein the physiological sensor is selected from a group comprising: an EKG monitor, a blood pressure monitor, an ETCO2 monitor, a pulse oximeter.

18. A system as in claim 15, further comprising the remote data collection system, wherein the remote data collection system comprises:
a first receiver in wireless communication with the transmitter to receive information indicative of the contents of a medication container, time of medication administration and fluid delivery characteristics;
a processor to calculate fluid volume based on fluid delivery characteristic information;
a memory element wherein medication injection information is time stamped and stored;
a communication channel capable of transferring stored data to a medical information system; and
a power source.

19. A system as in claim 18, wherein one or more of the following elements are part of a cellular phone: receiver, processor, memory, communication channel, power source.

20. A system comprising:
a housing comprising: a reusable sub-housing and a disposable sub-housing, the reusable sub-housing being operatively coupled to the disposable sub-housing, wherein the reusable sub-housing is intended for use by a plurality of patients and the disposable sub-housing is intended for use by a single patient;
a medication port extending from an external face of the housing and disposed within the disposable sub-housing, the medication port being configured to be fluidically coupled to a fluid outlet of a manually injectable medication container;
an identification sensor disposed within the reusable sub-housing to generate identification information indicative of contents of the medication container when the fluid outlet of the medication container is being fluidically coupled to the medication port;
a transmitter disposed within the reusable sub-housing and in communication with the identification sensor to wirelessly transmit the information generated by the identification sensor to a remote data collection system; and
a power source disposed within the reusable sub-housing powering the identification sensor and the transmitter.

21. A system as in claim 20, further comprising a junction element at least partially extending within the housing forming a first fluid channel and a second fluid channel, the first fluid channel extending from a first end to a second end, the second fluid channel extending from a distal end and terminating at the first fluid channel at an intersection intermediate the first end and the second end.

22. A system as in claim 20, wherein the transmitter is disposed within the reusable sub-housing.

23. A system as in claim 20, wherein the transmitter is a transceiver.

24. A system as in claim 20, wherein the disposable sub-housing is part of a kit including a sterile pouch enveloping the disposable sub-housing.

25. A system as in claim 20, wherein the first fluid channel and the second fluid channel are disposed within the disposable sub-housing.

26. A system as in claim 21, further comprising: a self-contained fluid delivery sensor disposed within the reusable sub-housing and in communication with the transmitter to characterize fluid flow through one or more of the first fluid channel and the second fluid channel, wherein the transmitter further wirelessly transmits data characterizing fluid delivery to the remote data collection system.

27. A system as in claim 20, further comprising: a processor disposed within the reusable sub-housing that is coupled to one or more of the identification sensor, the transmitter, and the power source.

28. A system as in claim 20, wherein the power source is self-contained, coupled to a remote power source, or is a rechargeable battery that can be detachably coupled to a remote charging source.

29. A system as in claim 20, wherein the housing has a shape and size enabling it to be held by a first hand of a user while the user administers medication from the medication container via the medication port using his or her second hand.

30. A system as in claim 20, wherein the reusable sub-housing is operatively coupled to the disposable sub-housing by a connection interface.

31. A system as in claim 30, wherein the connection interface includes one or more of an electrical contact, an optical coupling, a mechanical coupling, and a magnetic coupling.

32. A system as in claim 20, wherein the medication port and at least one fluid channel internally coupled to the port is disposed within the disposable sub-housing.

33. A system as in claim 20, further comprising: the remote data collection system, wherein the remote data collection system comprises:
a first receiver in wireless communication with the transmitter to receive information indicative of the contents of a medication container, time of medication administration and fluid delivery characteristics;
a processor to calculate fluid volume based on fluid delivery characteristic information;
a memory element wherein medication injection information is time stamped and stored;
a communication channel capable of transferring stored data to a medical information system; and
a power source.

34. A system as in claim 20, wherein one or more of the following elements are part of a cellular phone: receiver, processor, memory, communication channel, power source.

* * * * *